(12) United States Patent
High

(10) Patent No.: US 8,303,544 B2
(45) Date of Patent: Nov. 6, 2012

(54) CYSTOTOMY CATHETER CAPTURE DEVICE

(75) Inventor: Kenneth A. High, Helena, MT (US)

(73) Assignee: Swan Valley Medical Incorporated, Bigfork, MO (US)

( * ) Notice: Subject to any disclaimer, the term of this patent is extended or adjusted under 35 U.S.C. 154(b) by 0 days.

(21) Appl. No.: 13/181,260

(22) Filed: Jul. 12, 2011

(65) Prior Publication Data

US 2011/0276073 A1 Nov. 10, 2011

Related U.S. Application Data

(60) Division of application No. 12/061,250, filed on Apr. 2, 2008, now Pat. No. 8,002,764, which is a division of application No. 11/035,486, filed on Jan. 15, 2005, now abandoned, which is a continuation-in-part of application No. 10/837,879, filed on May 3, 2004, now abandoned.

(60) Provisional application No. 60/466,959, filed on May 1, 2003.

(51) Int. Cl.
*A61M 5/178* (2006.01)

(52) U.S. Cl. ............ 604/164.13; 604/164.01; 604/506; 604/910

(58) Field of Classification Search .................. 604/506, 604/164.01, 164.13, 514, 517, 910; 600/29, 600/30
See application file for complete search history.

(56) References Cited

U.S. PATENT DOCUMENTS 5,139,486 A * 8/1992 Moss ....................... 604/164.01

FOREIGN PATENT DOCUMENTS

DE 3919740 A1 * 12/1990

* cited by examiner

*Primary Examiner* — Laura Bouchelle
(74) *Attorney, Agent, or Firm* — John R. Ley

(57) ABSTRACT

A catheter capture device comprising a urethral sound and a sleeve that utilizes balloon inflation to capture the catheter. A catheter capture device comprising a urethral sound and a clamshell device. The clamshell device comprises two halves, one of which comprises two pins. One pin passes through the lateral holes in the tip of the catheter, and the other pin fits into a notch in the bottom half of the clamshell device. A catheter capture device comprising a urethral sound, a sleeve and a pin that passes through the lateral holes in the tip of the catheter. A catheter capture device comprising a urethral sound, a wire and a nodule, wherein the nodule captures the catheter by lodging in the tip of the catheter. The nodule could be a ball, hook, crimped wire or similar object. A method of capturing a catheter in an obese or non-obese patient.

13 Claims, 21 Drawing Sheets

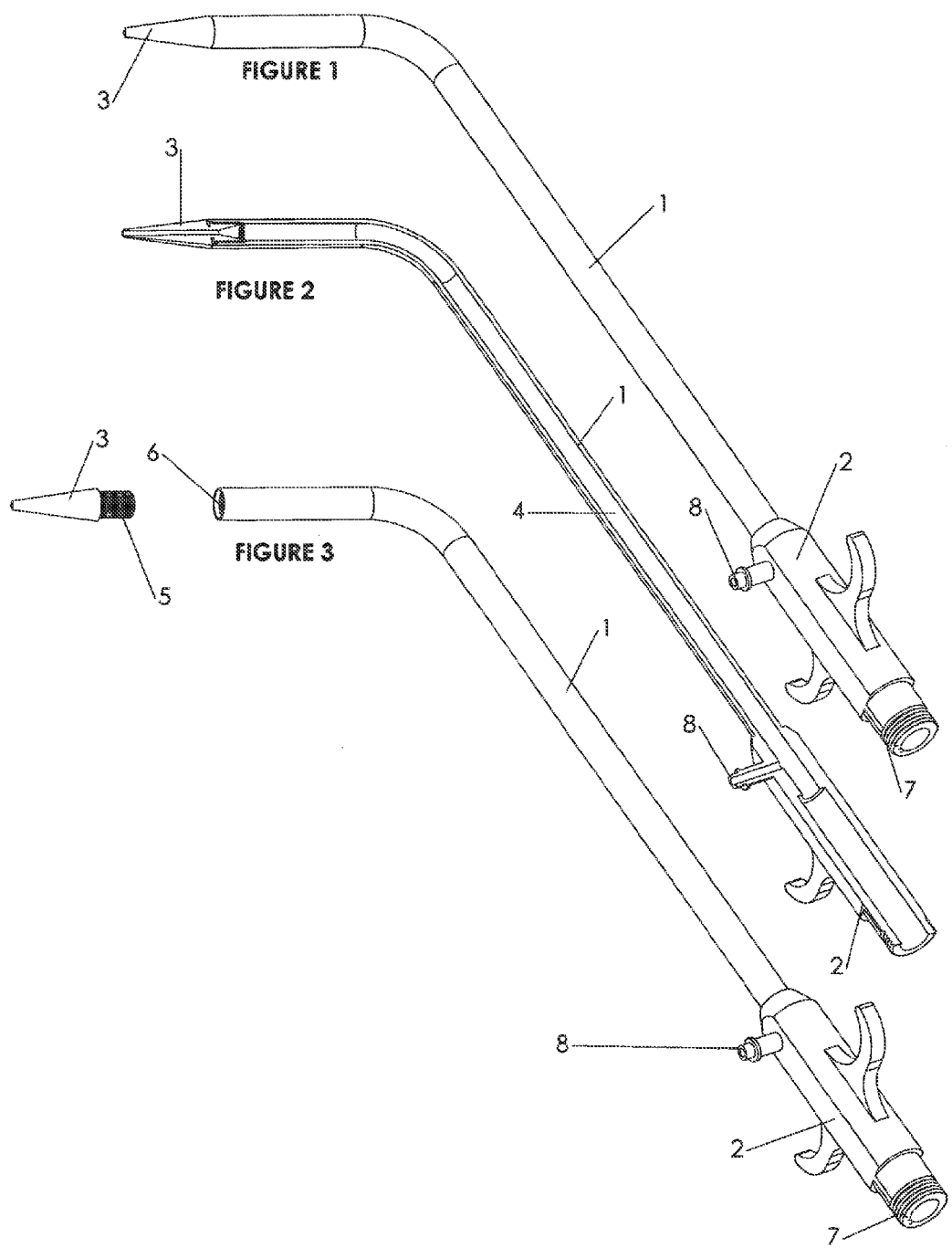

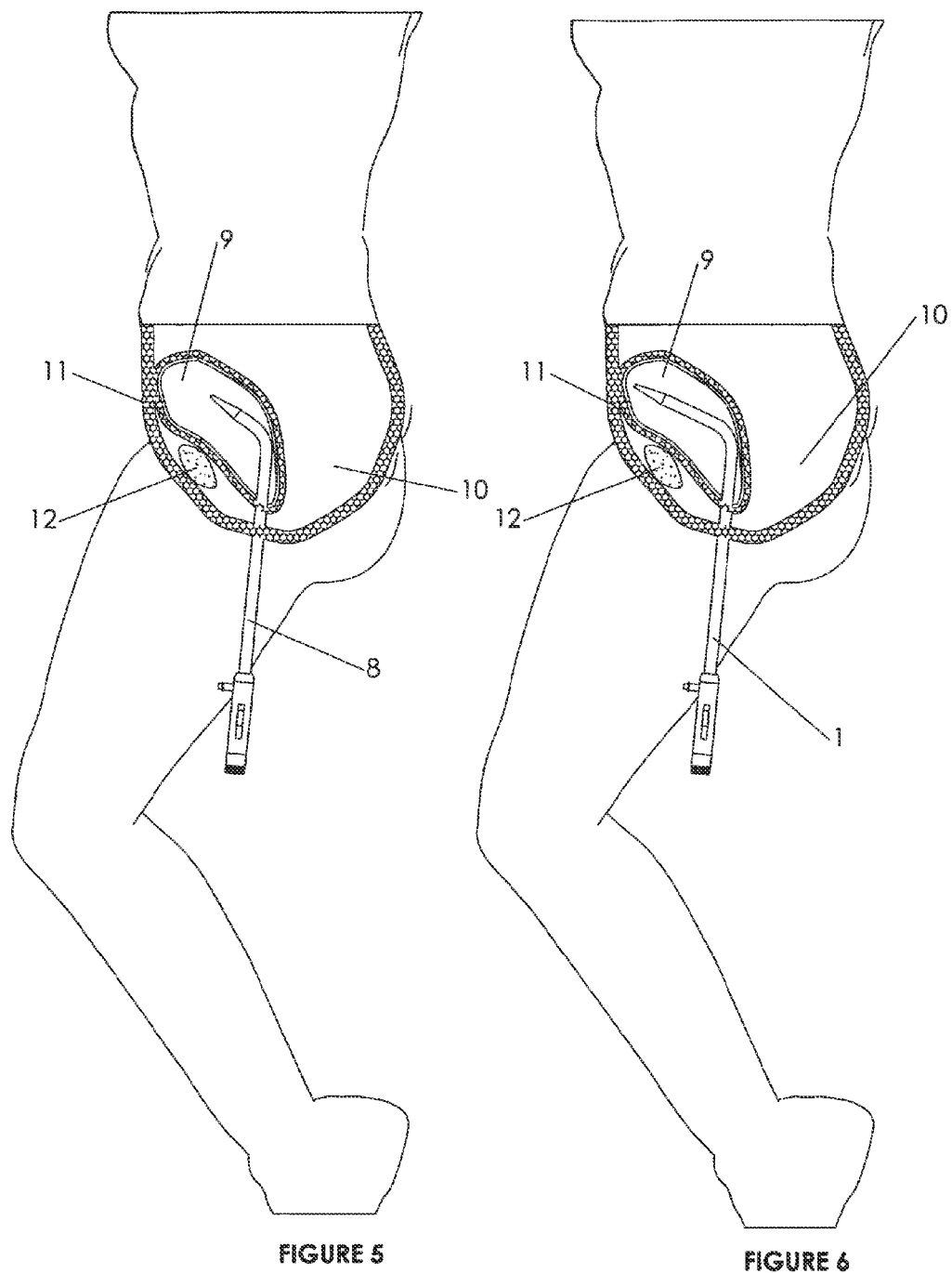

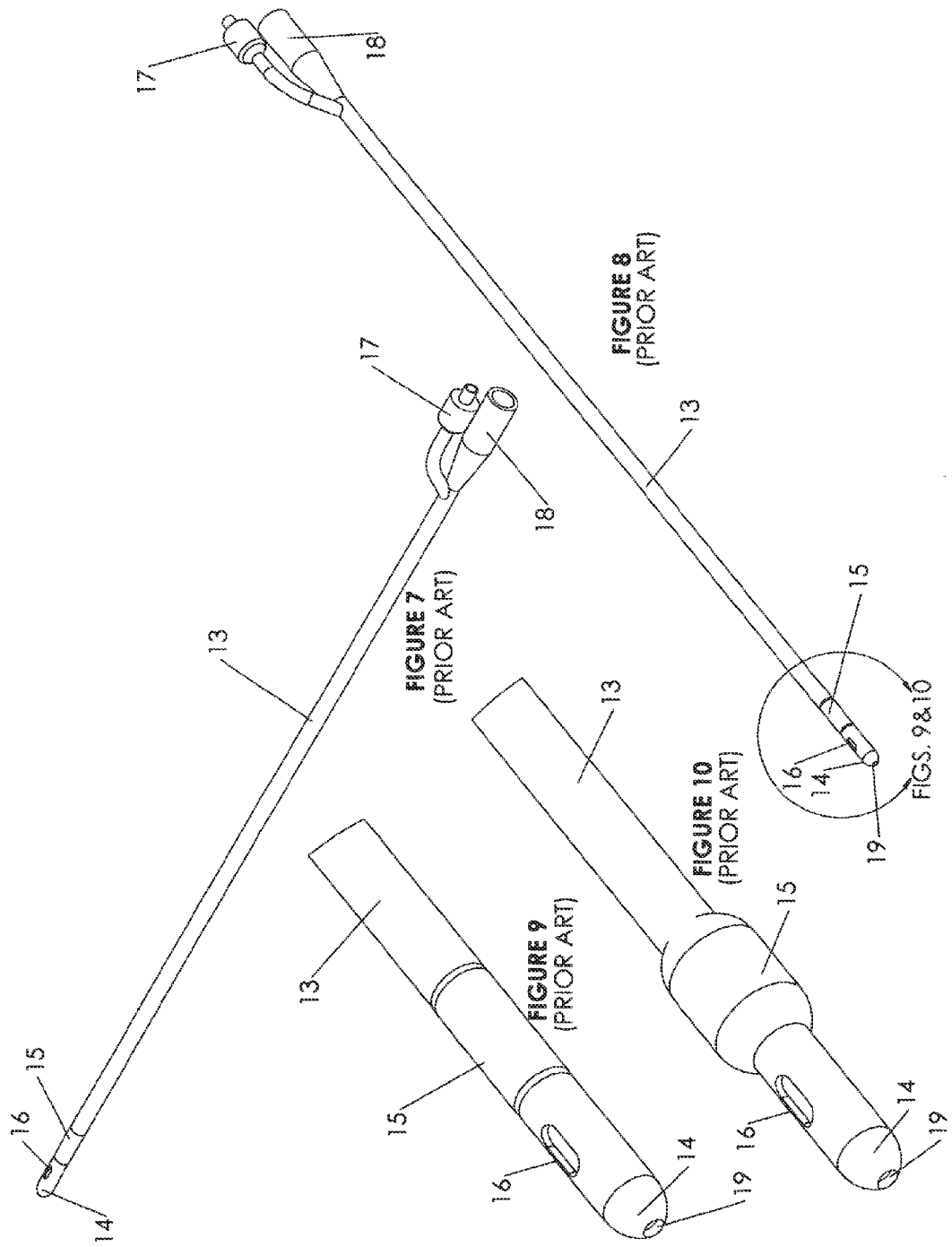

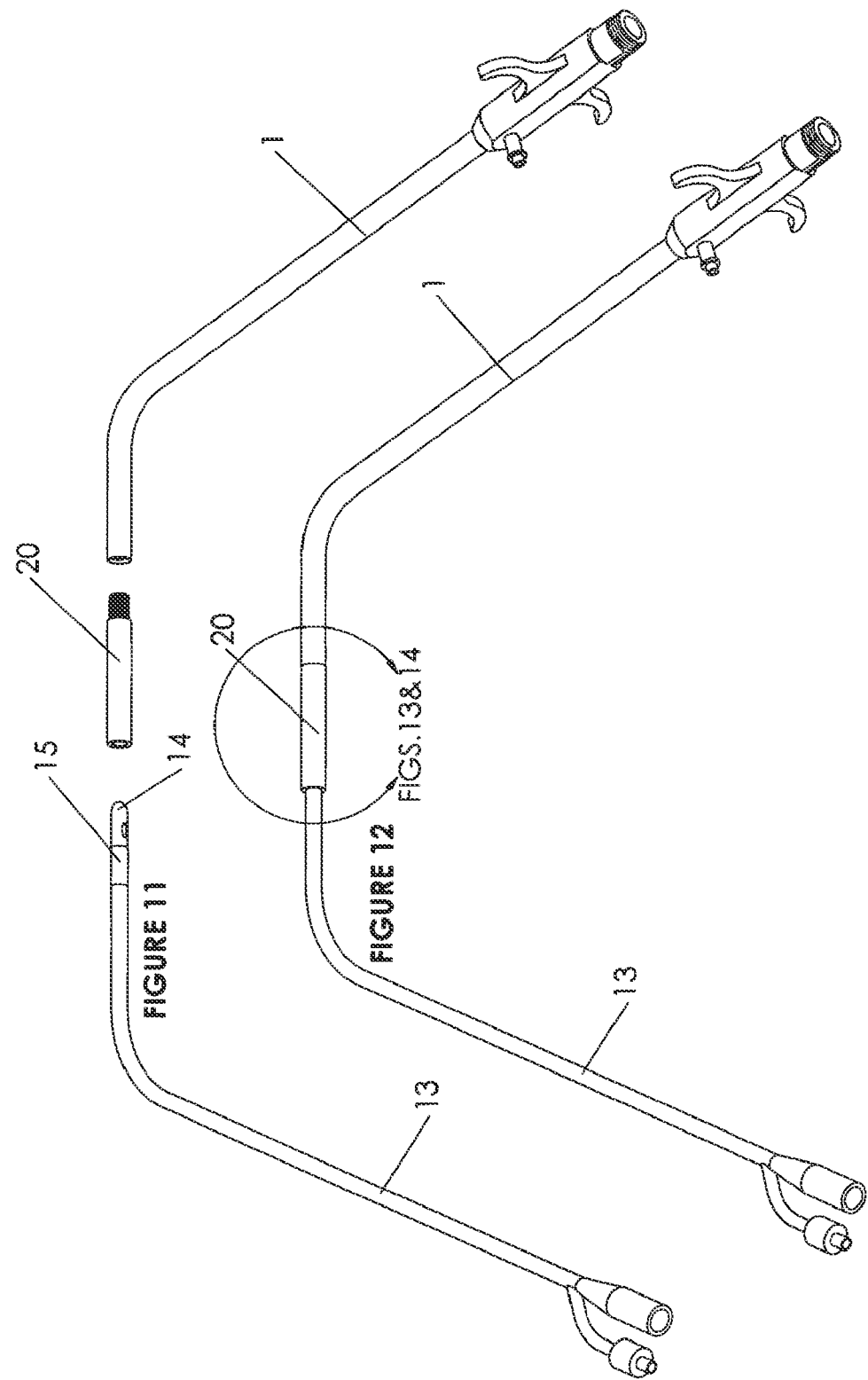

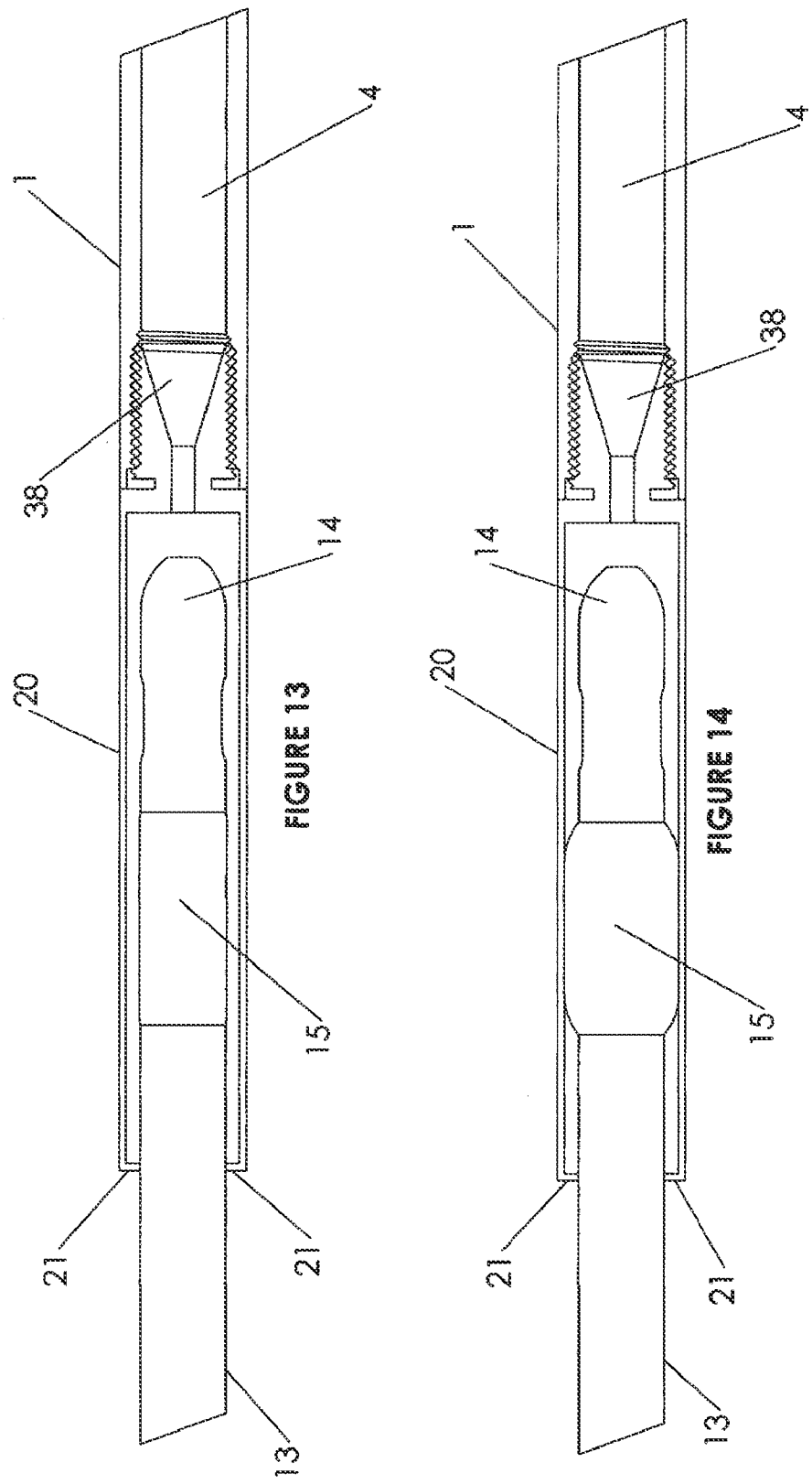

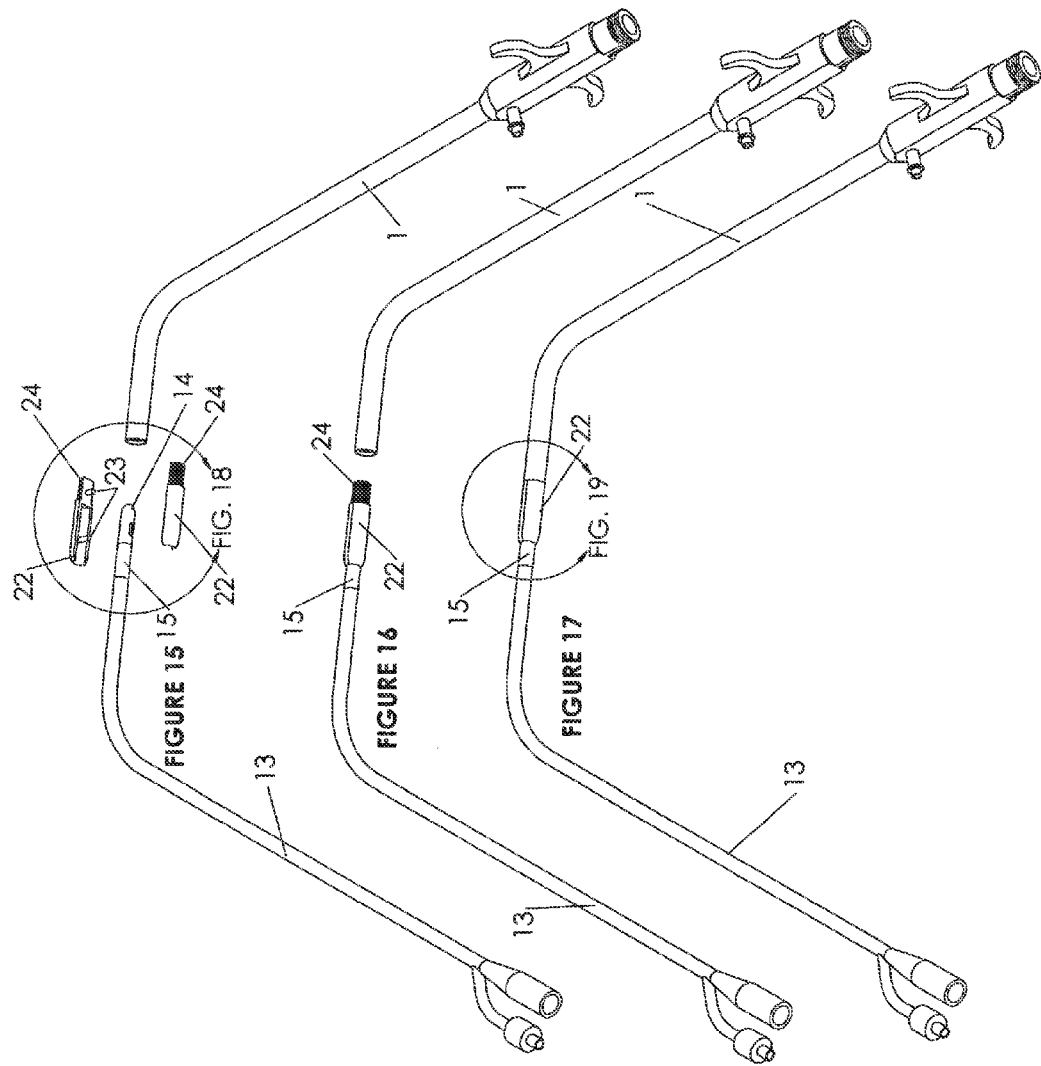

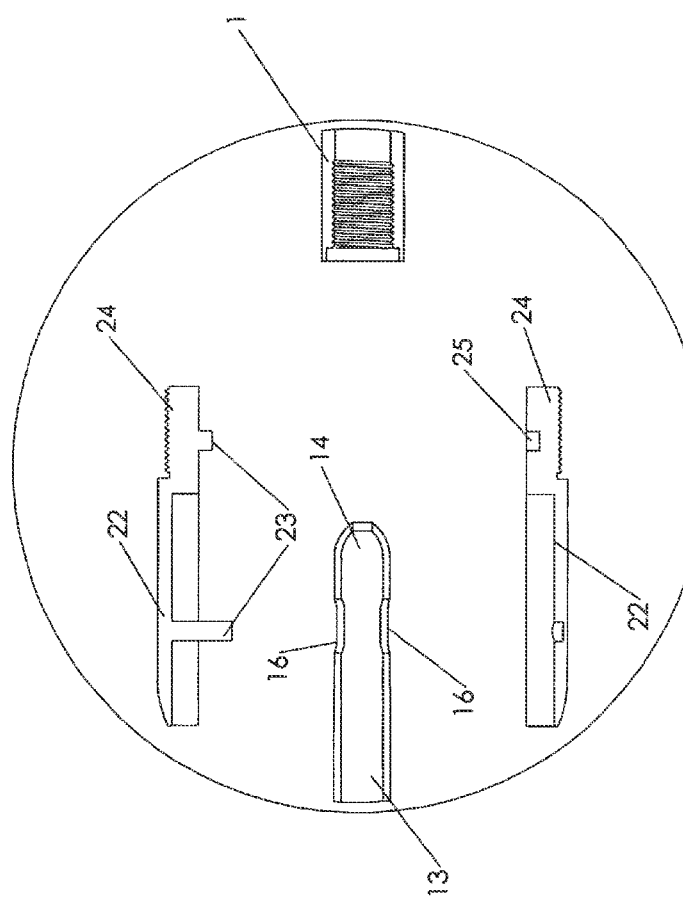
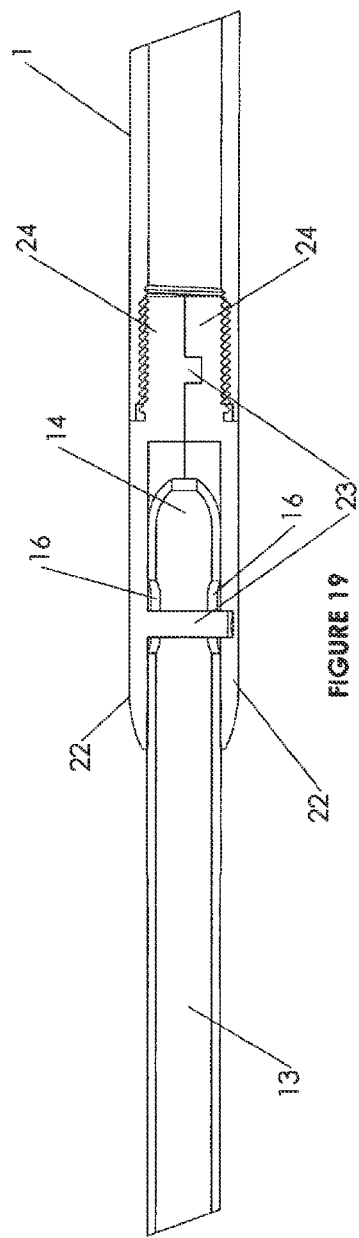

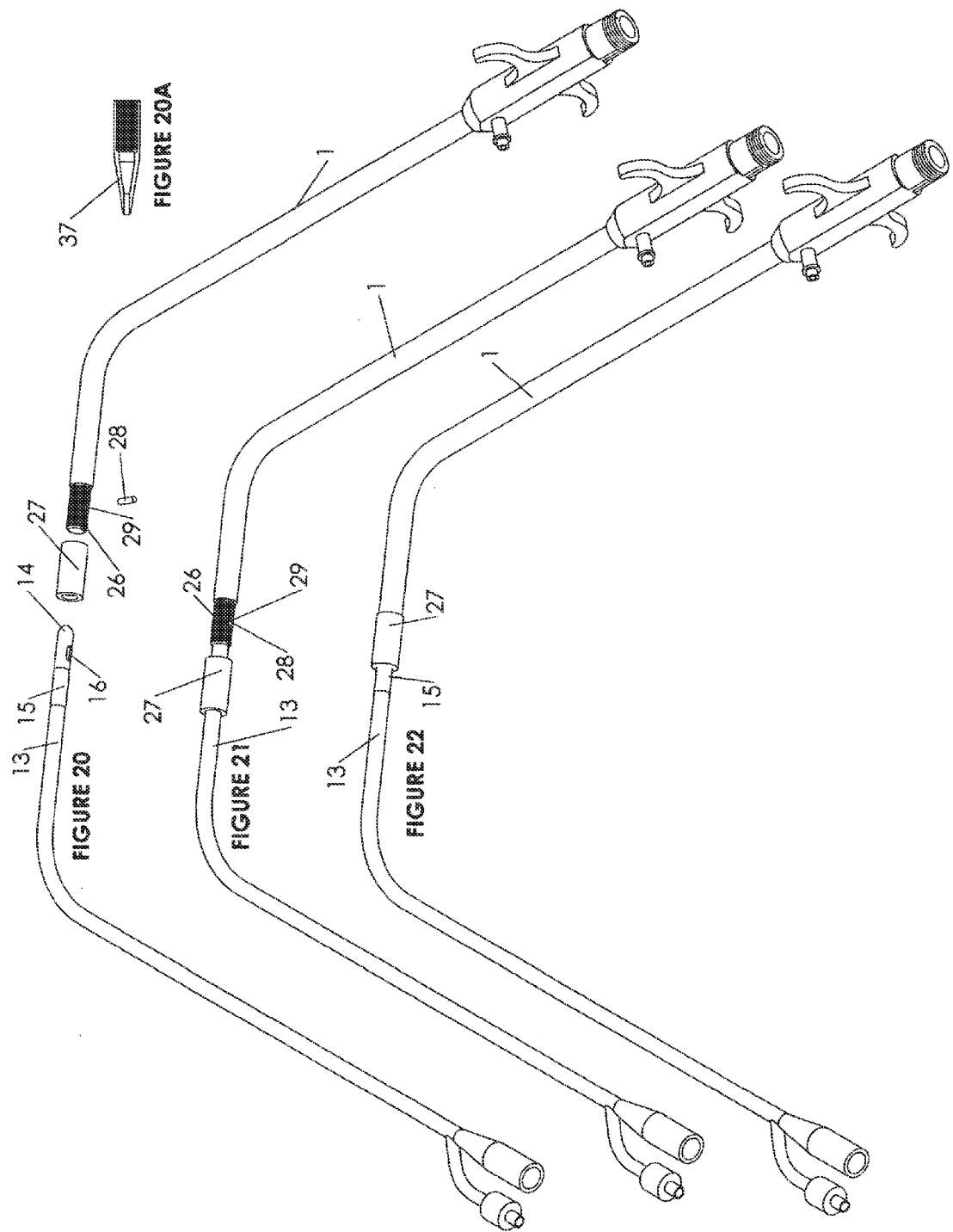

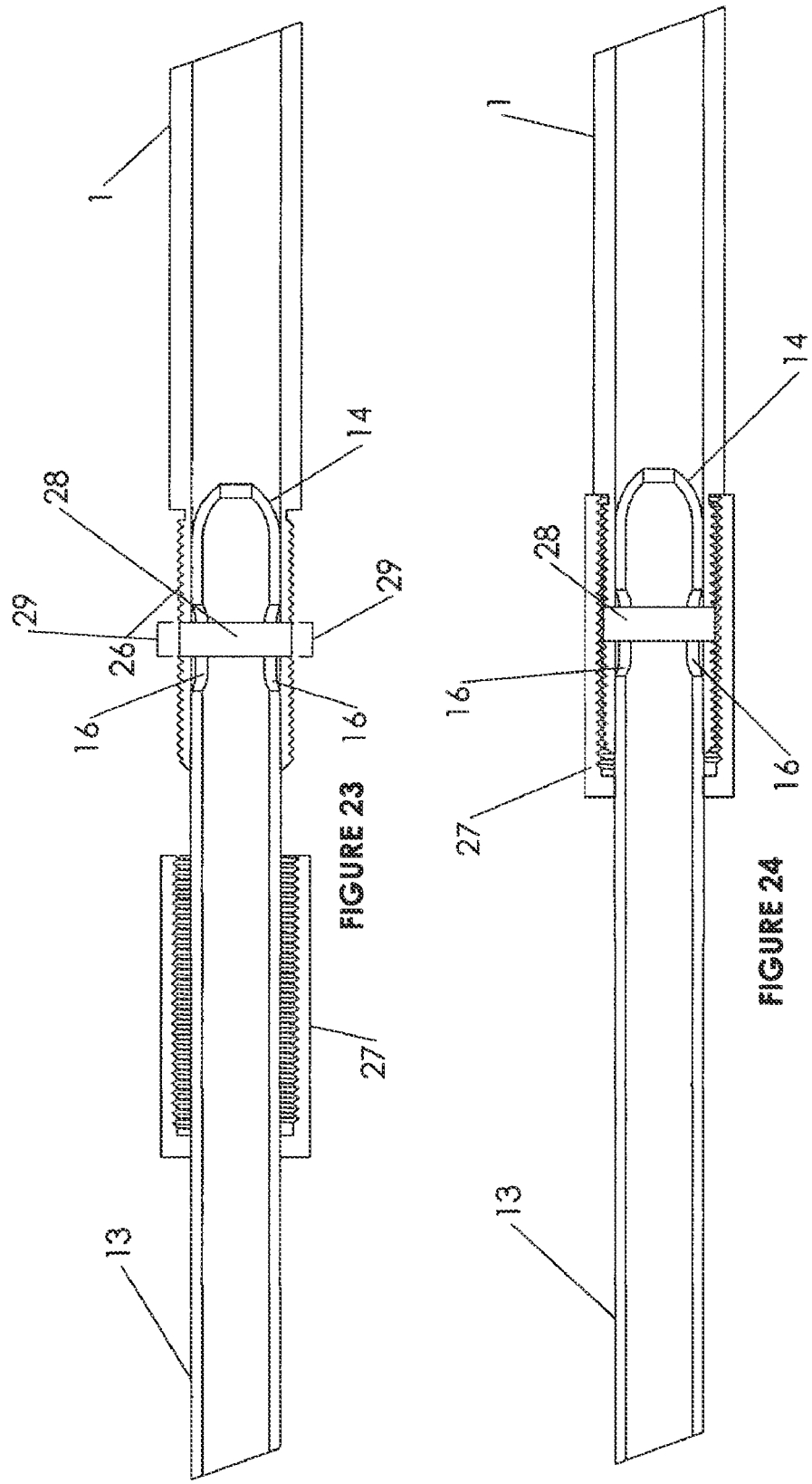

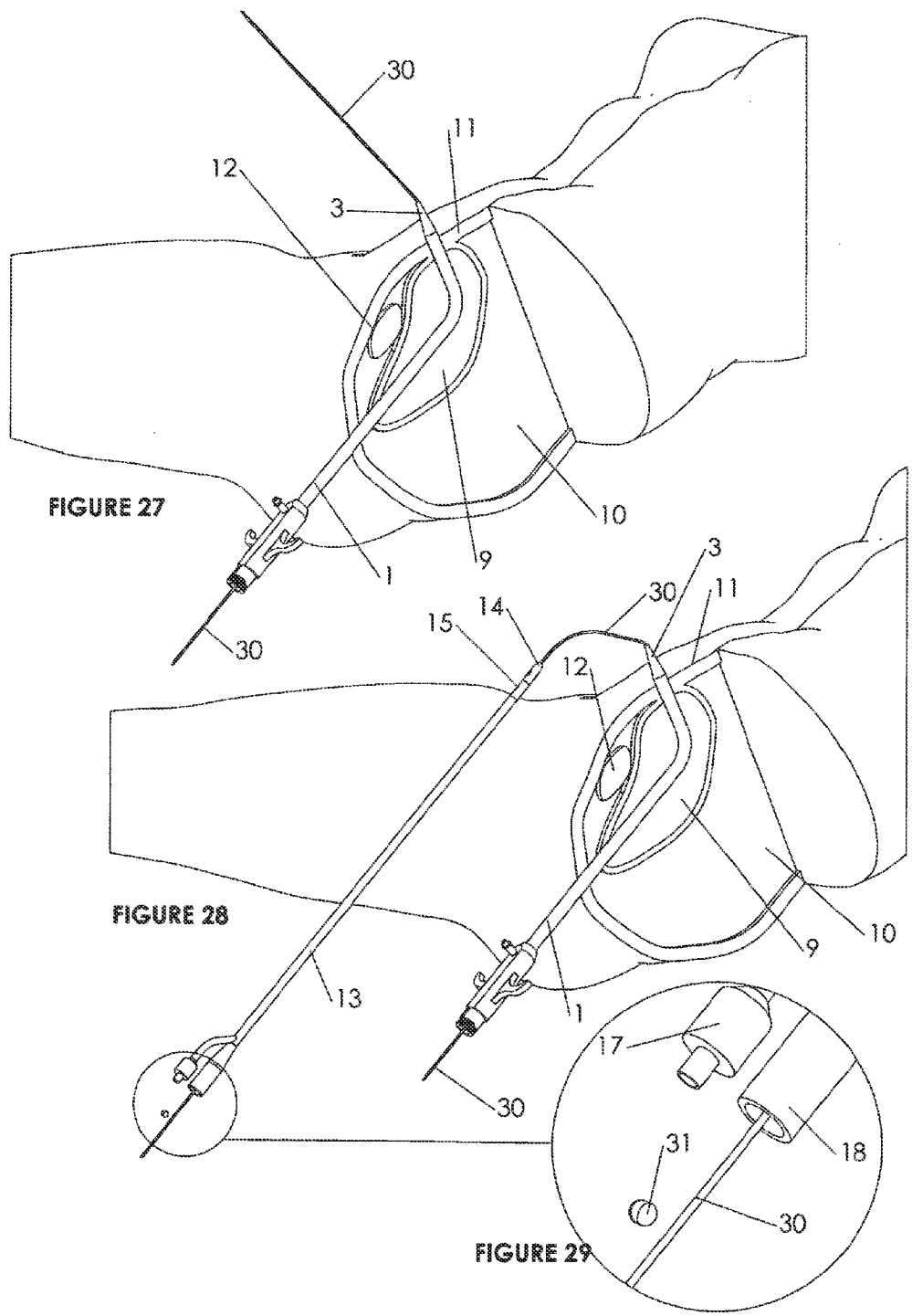

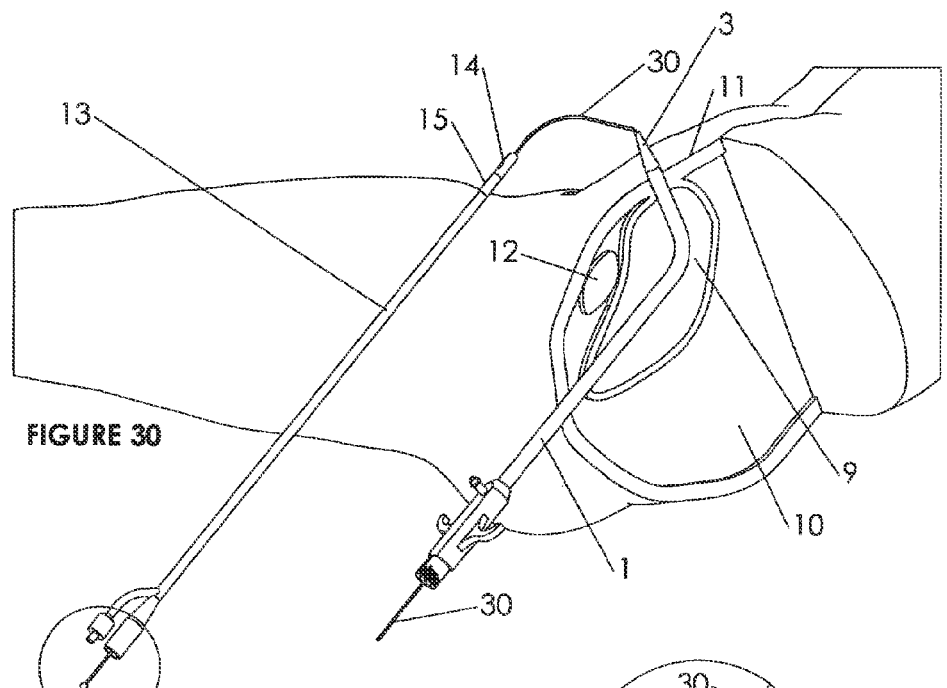
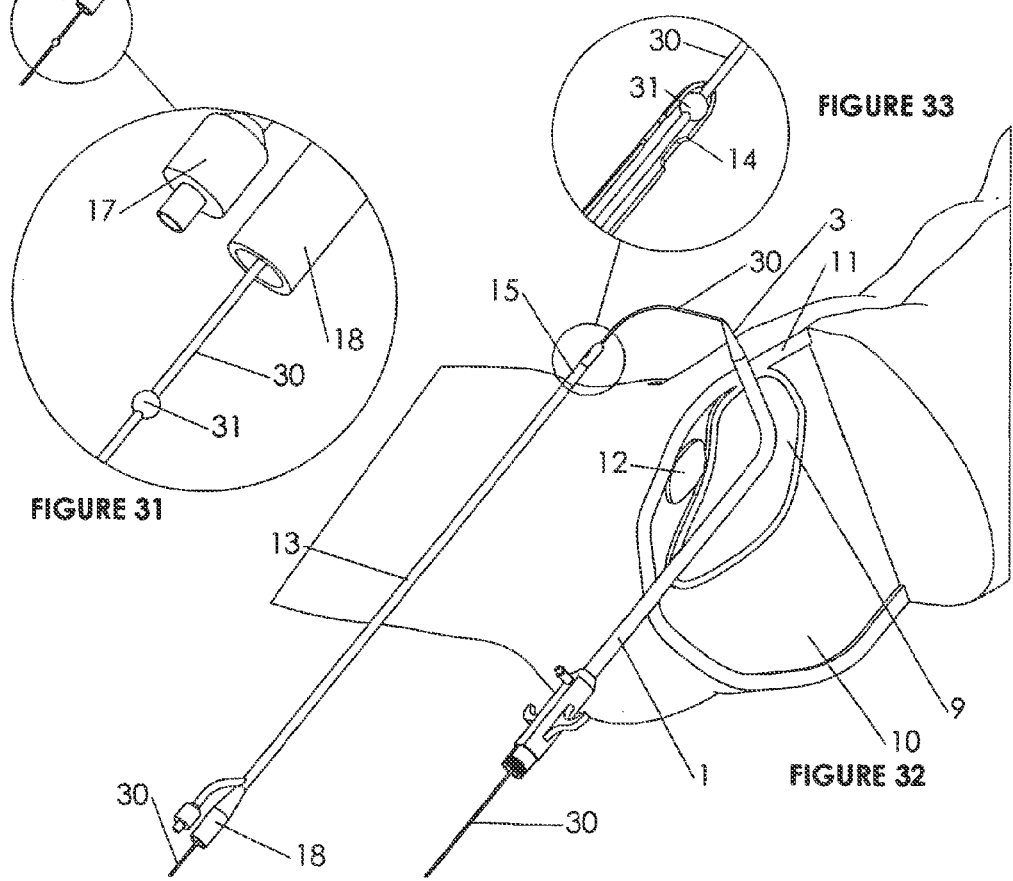

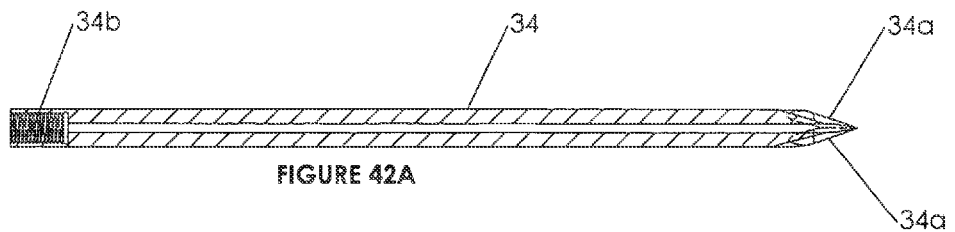
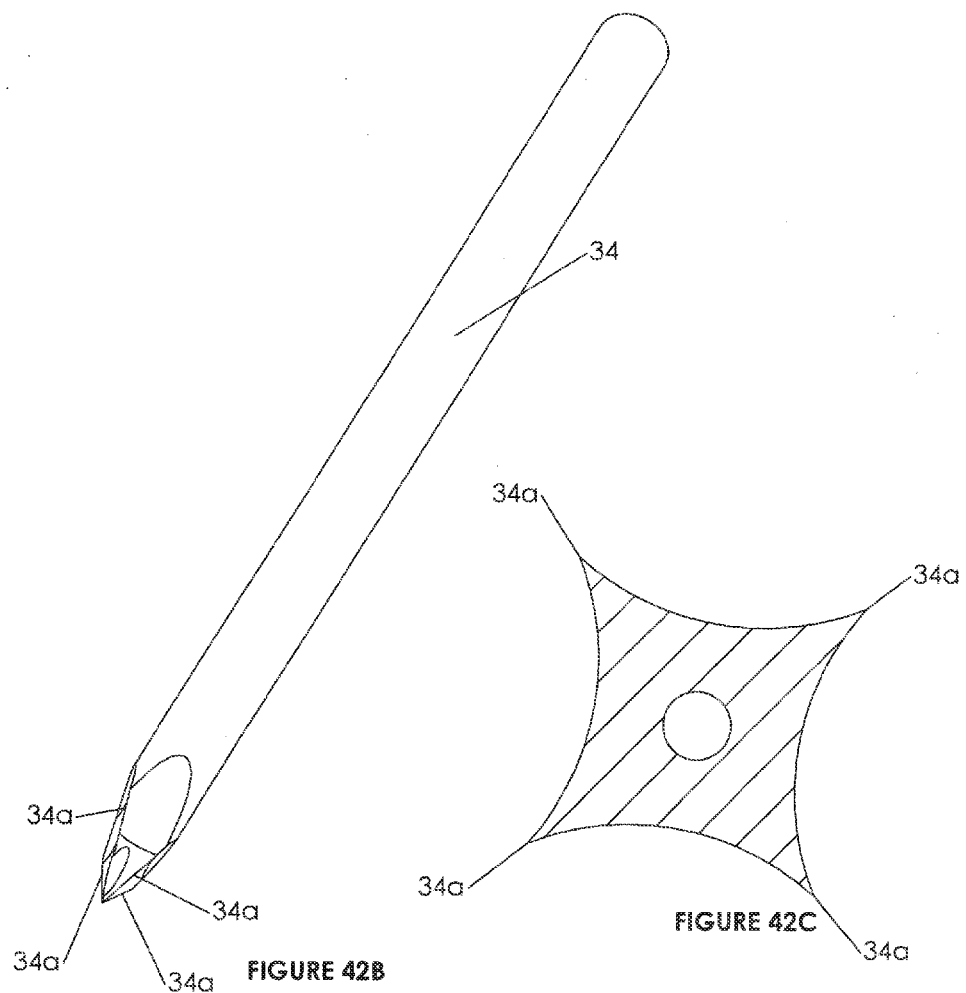

CYSTOTOMY CATHETER CAPTURE DEVICE

CROSS REFERENCE TO RELATED APPLICATIONS

This application is a division of U.S. application Ser. No. 12/061,250, filed Apr. 2, 2008, now U.S. Pat. No. 8,002,764, which is a division of U.S. application Ser. No. 11/035,486, filed Jan. 15, 2005, now abandoned, which is a continuation-in-part of U.S. application Ser. No. 10/837,879, filed May 3, 2004, now abandoned, which claims the benefit of U.S. provisional application 60/466,959, filed May 1, 2003, all of which are incorporated herein in their entirety.

FIELD OF THE INVENTION

The present invention relates to the field of medical devices, and more particularly, to a device that facilitates suprapubic catheter placement, even in the morbidly obese, in connection with vaginal surgeries for stress urinary incontinence and pelvic prolapse. The catheter capture device of the present invention can also be used for permanent suprapubic catheterizations in those situations in which patients suffer from incurable incontinence or urinary retention. The catheter capture device of the present invention includes both standard (reusable) and disposable embodiments.

BACKGROUND OF THE INVENTION

A million surgical procedures are performed annually to correct stress urinary incontinence (SUI) in 400,000 American women and 600,000 women abroad. In this context, "stress" refers to sneezing, straining and similar actions that can cause incontinence. A large percentage of these women are unable to void satisfactorily post-operatively and require a catheter to drain the bladder for several days or weeks. Post-operative urinary retention (PUR) occurs in up to forty-one percent (41%) of cases (1, 2). PUR is generally only a temporary event lasting a few days to weeks, but it can be painful, frightening and distressing, and it can complicate postoperative care. In these situations, the suprapubic catheter placed inside-out (I/O)—by passing a sound through the urethra, bladder and abdomen, attaching a catheter to the sound, bringing the catheter into the bladder, and connecting the catheter to drainage—is superior to all other methods. This procedure (called "suprapubic cystotomy") is almost always performed during surgery as opposed to post-operatively because it would require anesthesia and return to the operating room for a second operation.

Suprapubic catheterization may also be necessary with surgeries involving repair of pelvic prolapse, which refers to relaxation of the pelvic floor in a female patient and the descensus or drooping of the bladder, urethra, rectum and/or uterus—whether or not the patient also requires SUI surgery. Approximately seventy percent (70%) of women who undergo SUI surgery also require reconstructive vaginal surgery for repair of pelvic prolapse (3). Thirty percent (30%) of women in the United States and other developed countries experience pelvic prolapse at some point in their lives, and eleven percent (11%) of all women with this condition will require surgery to correct it. Twenty-nine percent (29%) of women who are operated on for prolapse repair will require repeat surgery (4). As these numbers illustrate, the need for a fast and reliable catheter capture method in women undergoing surgery to correct SUI and/or pelvic prolapse is widespread.

When a well functioning suprapubic catheter is in place, accurate post-operative evaluation of bladder recovery and emptying is relatively easy. A typical procedure involves leaving the suprapubic catheter plugged for the first two to three postoperative weeks so that the patient can attempt to void normally and the residual urine can be checked without discomfort. Residual urine is checked by keeping the suprapubic catheter clamped so that the bladder will fill, having the patient void when she feels the need to void, and then removing the plug from the catheter and measuring the urine that drains out of the catheter. When the post-void residual urine is consistently less than 60 ml, the catheter may be removed safely because it is highly unlikely the patient will develop (or redevelop) urinary retention. If urinary retention is still present two to three weeks after surgery, then the catheter can be removed and intermittent self-catheterization (ISC) commenced (5).

ISC is used in one of two situations: (1) when the patient has failed the post-operative trial of voiding and the suprapubic catheter has been removed; or (2) immediately after surgery when a suprapubic catheter was not used. In the former situation, when the patient remains unable to void satisfactorily two to three weeks after surgery, the suprapubic catheter is usually removed, and the patient begins ISC three to four times daily after voiding. With ISC, a new catheter is passed by the patient through the urethra into the bladder each time she voids (to measure the residual urine). When post-void residual urines are low, the patient is free to return to normal voiding without catheters.

The preferred approach is to teach the patient pre-operatively to perform ISC three to four times daily. Many women, however, are either unable to learn or do not want to place a catheter blindly into the urethra and bladder, through a painful, freshly operated area with sutures that are oozing blood and serum (5). The developed consensus among medical practitioners is to place a suprapubic catheter at surgery if the patient has not demonstrated her ability or willingness to perform ISC (1, 6). Passage of a suprapubic catheter from the inside-out (I/O) during surgery is believed to be the best solution because it is safer than passing a catheter from the outside-in (O/I). Furthermore, the I/O technique allows physicians to use larger catheters, which are more reliable in terms of draining the urine. Smaller catheters (i.e., catheters with a smaller diameter—not length) are used with the O/I techniques because O/I can cause perforation of the bowel or peritoneal cavity, and larger tubes (or catheters) would lead to a higher complication rate. The I/O method, despite its advantages, has been awkward and difficult with current devices.

The most commonly employed technique is outside-in (O/I) suprapubic "punch" cystotomy, which entails passage of a small (width) catheter through a small trocar that is "punched" through the abdomen into the bladder. In comparison to I/O techniques, the O/I technique is simple, cheap and easy, but bladder drainage is unreliable because the small catheters often kink or become obstructed when small blood clots enter or form inside the catheter. As a result, the O/I technique is never used for permanent catheterization because of unreliable urine drainage. All O/I devices are more prone to unrecognized bowel or peritoneal perforation with serious secondary complications than the I/O devices. For these reasons, the O/I technique has been condemned by Drs. Ed McGuire and J. Q. Clemens in Campbell's Urology, 8.sup.th edition, p. 1160. The applicant believes that an important reason for the current popularity of O/I techniques is because the I/O devices that are currently available are poorly designed, awkward and difficult to use. Moreover, catheter capture is difficult to achieve with these I/O devices.

Currently, the safest and the only reliable method for inserting I/O catheters is to pass a hollow stainless steel device (called a "sound") through the urethra and bladder and then through the abdominal wall, at which point the catheter is affixed to the sound and drawn back into the bladder. The catheter is then inflated and connected to drainage. Each of the devices currently on the market, however, has serious drawbacks. One drawback that is common to all of these devices is that the tip of each device has a short "throw" so that it is difficult to pass the tip of the device through the abdominal wall. When the device is too short to advance through the abdominal wall, catheter capture (i.e., securing or affixing the catheter) becomes extremely difficult. Another drawback is that existing catheter capture methods do not work. If the catheter cannot be captured, then the physician will have to insert an indwelling urethral Foley catheter immediately after surgery, or the surgeon will have to make an incision through the abdomen and into the bladder in order to place the suprapubic catheter. Despite the flaws in current technology, there have been no significant developments in catheter placement devices for more than twenty (20) years, although there are a number of patents in this area.

U.S. Pat. No. 5,152,749 (Giesy et al., 1992), U.S. Pat. No. 5,232,443 (Leach, 1993) and U.S. Pat. No. 5,348,541 (Lyell, 1994) all describe suprapubic catheter placement devices. The Giesy device is limited in that it only describes two means of coupling the catheter to the placement device. These two means are (i) a loop on the catheter and an indentation on the placement device and (ii) a ball and stem on the catheter that fit into a groove and cavity on the placement device. A sheath slides over the device to hold the coupling mechanism in place. The Leach device is limited in that it has a short "throw" and uses a jaw mechanism to capture the catheter. The jaw mechanism becomes wider after the catheter is enclosed within the jaws, making it more difficult for the catheter to be pulled safely through a small hole in the bladder and potentially resulting in loss of the catheter. Loss of the catheter requires the surgeon to start all over again, subjecting the patient to further unnecessary trauma. The Lyell device is limited in that the only catheter capture means it describes is a hook on the end of a flexible wire. The hook couples with the lateral hole provided in the catheter—not with the hole that extends longitudinally at the tip of the catheter, as in one embodiment of the present invention. The various embodiments of the present invention are superior to the embodiments described above in terms of efficacy and ease of use.

Because of the problems associated with current suprapubic catheter placement technologies, many patients have been placed on urethral catheterization immediately after surgery instead of suprapubic bladder catheterization during surgery. Urethral catheterization involves placing the catheter directly into the bladder through the urethra. Urethral catheterization is simpler, cheaper and easier than suprapubic catheterization, but it has its disadvantages. Specifically, residual urine is impossible to determine while an indwelling urethral catheter is present to drain the bladder because the catheter fills the urethra and makes it impossible to void. Patients are much more comfortable with suprapubic catheters than with urethral catheters exiting the genitalia, and sexual relations are impossible with a urethral catheter in place. Thus, the preferred alternative is still I/O suprapubic catheter placement, but current methods and available devices are inadequate—particularly in cases involving women, where the distance from the bladder to the abdominal is often greater than in men.

Although designed initially to solve problems relating to the use of other catheter placement devices in women, the catheter capture device of the present invention can be used with both women and men. Suprapubic catheterization is often indicated for those men and women who are unable to empty their bladders or who have lost control of their bladders and are required to live in diapers—patients found commonly in nursing homes. These patients include men with high-grade prostate obstruction and men and women with neurologic diseases (such as multiple sclerosis, stroke, Parkinson's disease, Alzheimer's disease and senility) that destroy bladder control and bladder emptying. Most of these patients do not have suprapubic catheterization because it would be a difficult and formidable procedure for them as currently performed.

Accordingly, it is an object of the present invention to provide a fast and reliable method of capturing a suprapubic catheter for placement in the bladder. It is a further object of the present invention to provide a catheter capture device with a "throw" that is sufficiently long to pass through the bladder, abdominal wall and skin easily and rapidly. It is a further object of the present invention to provide a catheter capture device with a modified trocar tip that is suitable for passing over a wire, traversing the abdominal wall, and passing into the bladder. It is a further object of the present invention to provide a catheter capture device that can be used effectively in both women and men whenever suprapubic catheterization is indicated and an abdominal incision is not employed. It is a further object of the present invention to provide a catheter capture device that affords reliable long-term catheter drainage. It is a further object of the present invention to allow placement of permanent suprapubic catheters for chronically ill and elderly men and women instead of condemning them to diapers or long-term urethral catheterization in nursing homes. It is a further object of the present invention to provide a device and method for placing a suprapubic catheter in the morbidly obese. It is a further object of the present invention to provide a catheter capture device that is disposable.

SUMMARY OF THE INVENTION

According to one presently preferred aspect of the invention, a catheter capture device for releasably coupling an end of a sound to a tip of a catheter having an inflatable balloon is provided. The catheter capture device includes a sleeve having one end adapted for attachment to the end of the sound and another end with a hollow portion provided by an inner wall. The hollow portion is sized to receive the tip of the catheter and the balloon freely therein when the balloon is in a deflated state. The inner wall of the hollow portion is configured to frictionally engage the balloon when the balloon is in an inflated state to prevent relative movement between the balloon and the inner wall.

According to another presently preferred aspect of the invention, a catheter capture device includes a hollow sound having proximal and distal ends. The device further includes a catheter having proximal and distal ends with a balloon adjacent the distal end wherein the balloon is selectively inflatable and deflatable. Further yet, the device includes a hollow portion having a tubular inner wall adjacent the distal end of the sound. The hollow portion is sized to receive the balloon freely therein when the balloon is deflated. The inner wall of the hollow portion is configured to frictionally engage the balloon when the balloon is inflated to prevent relative movement between the balloon and the inner wall.

According to yet another presently preferred aspect of the invention, a method of releasably coupling a catheter having an inflatable balloon to a urethral sound is provided. The method includes providing a hollow portion having a tubular inner wall adjacent a distal end of the sound and inserting the catheter balloon into the hollow portion when the balloon is substantially deflated. Then, inflating the balloon within the hollow portion to releasably couple the catheter to the sound.

According to yet a further aspect of the invention, a method of forming a surgical opening through an abdomen and into a bladder is provided. The method includes inserting a hollow sound though a urethra and positioning a tip of the sound against a wall of the bladder. Then, passing a wire through the sound and penetrating the bladder wall and then the abdomen with the wire and exposing a portion of the wire externally from the abdomen. Next, sliding a hollowed cutting tool over the exposed portion of the wire. Further, pushing and guiding the cutting tool through the abdomen and then through the bladder wall along the guided path of the wire to form the surgical opening. Lastly, removing the cutting tool outwardly from the bladder through the surgical opening.

BRIEF DESCRIPTION OF THE DRAWINGS

These and other aspects, features and advantages of this invention will become apparent from the following detailed description of the preferred embodiments and best mode, appended claims and accompanying drawings, in which:

FIG. 1 is a perspective view of the urethral sound of the present invention;

FIG. 2 is a section view of the urethral sound of the present invention;

FIG. 3 is a perspective view of the urethral sound of the present invention with the tip removed;

FIG. 5 is a section view of a urethral sound device inserted into the bladder of a patient. As compared to the sound shown in FIG. 6, this sound has a relatively shorter throw and a relatively greater angle;

FIG. 6 is a section view of the urethral sound of the present invention inserted into the bladder of a patient. As compared to the sound shown in FIG. 5, this sound has a relatively longer throw and a relatively smaller angle;

FIG. 7 is a perspective view of a Councill catheter;

FIG. 8 is a perspective view of Councill catheter;

FIG. 9 is a partial perspective view of the tip of a Councill catheter;

FIG. 10 is a partial perspective view of the tip of a Councill catheter with the balloon inflated;

FIG. 11 is a perspective view of the balloon capture embodiment of the present invention with the sleeve disconnected from the sound;

FIG. 12 is a perspective view of the balloon capture embodiment of the present invention with the sleeve connected to the sound;

FIG. 13 is a partial section view of the balloon capture embodiment of the present invention in which the balloon is deflated;

FIG. 14 is a partial section view of the balloon capture embodiment of the present invention in which the balloon is inflated;

FIG. 15 is a perspective view of the clamshell capture embodiment of the present invention in which the clamshell is disengaged from the catheter and from the sound;

FIG. 16 is a perspective view of the clamshell capture embodiment of the present invention in which the clamshell is closed over the catheter but not attached to the sound;

FIG. 17 is a perspective view of the clamshell capture embodiment of the present invention in which the clamshell is closed over the catheter and attached to the sound;

FIG. 18 is a section view of the clamshell and a partial section view of the catheter and sound;

FIG. 19 is a section view of the clamshell when it is closed over the catheter and attached to the sound (as shown in FIG. 17);

FIG. 20 is a perspective view of the sleeve capture embodiment of the present invention in which the catheter is not inserted into the threaded extension of the sound, and the sleeve is not installed over the threaded extension of the sound;

FIG. 20A is a section view of the removable tip of the sound for use with the sleeve capture embodiment of the present invention;

FIG. 21 is a perspective view of the sleeve capture embodiment of the present invention in which the catheter is inserted into the threaded extension of the sound, but the sleeve is not installed over the threaded extension of the sound;

FIG. 22 is a perspective view of the sleeve capture embodiment of the present invention in which the catheter is inserted into the threaded extension of the sound, and the sleeve is installed over the threaded extension of the sound;

FIG. 23 is a partial section view of the catheter inserted into the threaded extension of the sound and a section view of the sleeve positioned over the catheter but not over the threaded extension of the sound;

FIG. 24 is a partial section view of the catheter inserted into the threaded extension of the sound and a section view of the sleeve positioned over the threaded extension of the sound;

FIG. 27 is a section view of the urethral sound of the present invention with a wire passed through the sound;

FIG. 28 is a section view of the urethral sound of the present invention with a wire passed through the sound and a catheter on the wire;

FIG. 29 is a partial perspective view of the ball and wire;

FIG. 30 is a section view of the urethral sound of the present invention with a wire passed through the sound and a catheter and ball on the wire;

FIG. 31 is a partial perspective view of the ball on the wire;

FIG. 32 is a section view of the urethral sound of the present invention with a wire passed through the sound, a catheter and ball on the wire, and the ball pulled to the tip of the catheter;

FIG. 33 is a section view of the catheter tip with the ball on the wire and inside the catheter tip;

FIG. 42A is a section view of the trocar;

FIG. 42B is a perspective view of the trocar;

FIG. 42C is a section view of the trocar, showing the cut made by the trocar blades;

DETAILED DESCRIPTION

Figure 4:
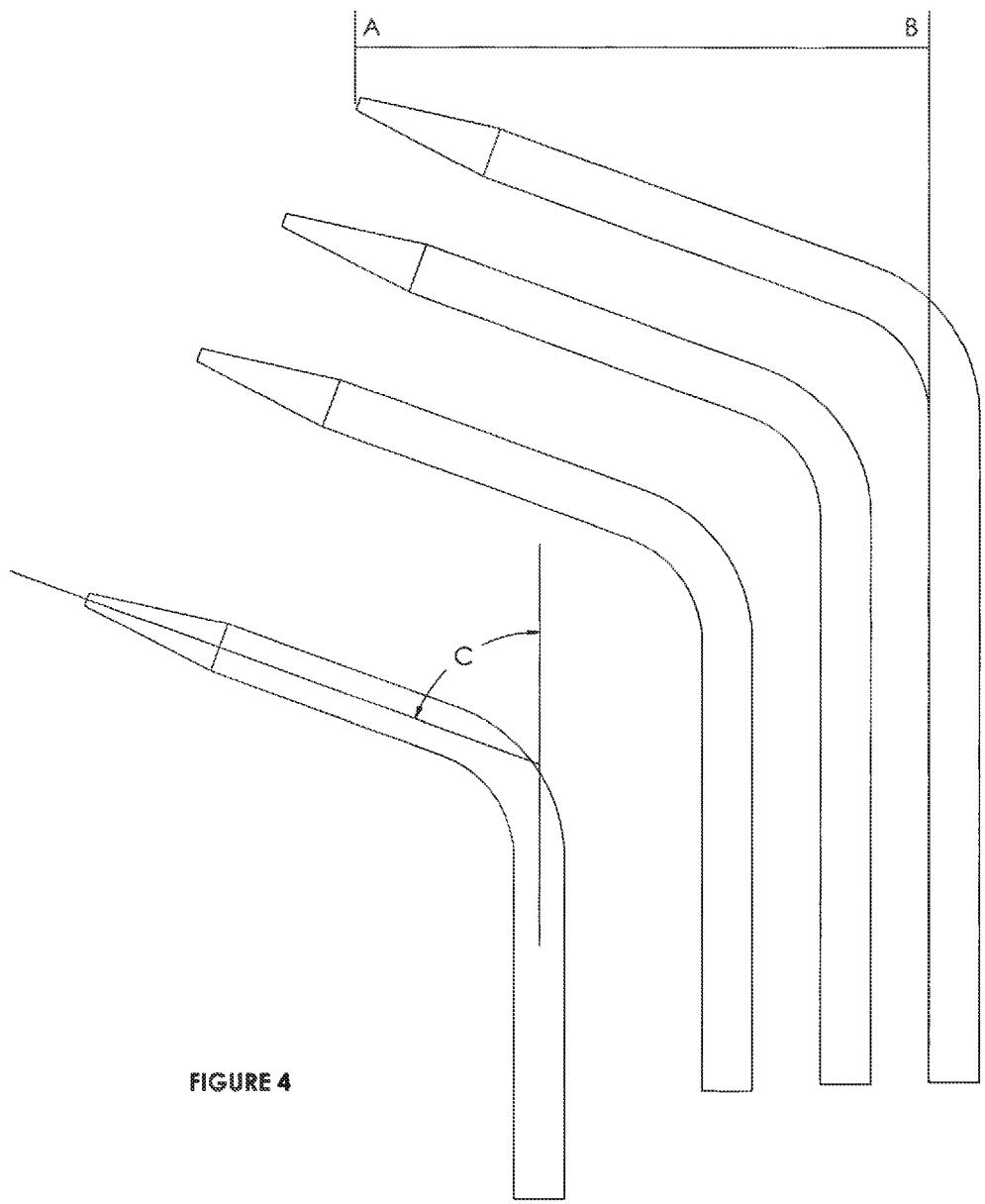
FIG. 4 is a partial schematic view of four different embodiments of the urethral sound of the present invention, illustrating different "throws" available.

Referring in more detail to the drawings, FIG. 1 is a perspective view of the urethral sound of the present invention. This figure shows the sound 1, the handle 2, and the tip 3. The sound is hollow, and there are holes at either end of the sound for the insertion of a wire.

FIG. 2 is a section view of the urethral sound of the present invention. This figure shows the sound 1, the handle 2, the tip 3, and the hollow channel 4, which extends from one end of the sound to the other.

FIG. 3 is a perspective view of the urethral sound of the present invention with the tip removed. This figure shows the sound 1, the handle 2, and the tip 3. It also shows the threaded end 5 of the tip, which is inserted into the threaded distal end 6 of the sound. The proximal end of the sound 7 is also threaded for the addition of a Tuohy-Borst adapter or an endoscopic cap.

FIG. 4 is a partial schematic view of four different embodiments of the urethral sound of the present invention, illustrating different "throws" available. The throw is defined in this figure as the distance from point A to point B. The sound of the present invention preferably has a throw that is at least six (6) centimeters long, although a shorter throw may be appropriate in certain situations. Different throw lengths may be useful for different types of patients (for example, male or female, adult or child). In this figure, the throw length increases from the sound shown at the bottom to the sound shown at the top. In practice, the throw will probably not be longer than fourteen (14) centimeters. The angle of the sound is shown as C. The angle of the sound is preferably in the range of sixty (60) to eighty (80) degrees. The angle of all of the sounds shown in this figure is seventy (70) degrees. FIGS. 5 and 6 illustrate the difference between a sound with a shorter throw and relatively greater angle (FIG. 5) and a sound with a longer throw and relatively smaller angle (FIG. 6).

FIG. 7 is a perspective view of a Councill catheter. Although the present invention can be used with many different types of catheters and is not limited to the Councill catheter (except for the ball-on-a-wire, hook-on-a-wire, nodule-on-a-wire and crimped wire embodiments), a drawing of the Councill catheter is provided for illustrative purposes. This figure shows the catheter shaft 13, the catheter tip 14, one of two lateral holes 16 in the catheter tip 14, and the uninflated balloon 15. On the proximal end of the catheter, the inflation member 17 and drainage connection 18 are also shown. The purpose of the inflation member 17 is to inflate the balloon 15 on the distal end of the catheter.

FIG. 8 is a perspective view of Councill catheter. As in FIG. 7, this figure shows the catheter shaft 13, the catheter tip 14, one of two lateral holes 16 in the catheter tip 14, and the balloon 15. It also shows a circular hole 19 at the end of the catheter tip 14. A Foley catheter is the same as the Councill catheter, except that it does not have this circular hole 19 in the catheter tip. In addition, this figure shows the inflation member 17 and drainage connection 18. The circle at the distal end of the catheter shows the orientation of FIGS. 9 and 10.

FIG. 9 is a partial perspective view of the tip of a Councill catheter. This figure shows the distal end of the catheter only, with the tip 14, balloon 15, one of two lateral holes 16, and the circular hole 19 in the catheter tip. FIG. 10 is a partial perspective view of the tip of a Councill catheter with the balloon 15 inflated.

FIGS. 11-14 illustrate the balloon capture embodiment of the present invention. FIG. 11 is a perspective view of the balloon capture embodiment of the present invention with the sleeve disconnected from the sound. This figure shows the sound 1, the catheter 13, the catheter tip 14, and the balloon 15. It also shows a sleeve 20, which is threaded at one end so that it can be inserted into the threaded distal end of the sound, where the tip (not shown) would normally attach.

FIG. 12 is a perspective view of the balloon capture embodiment of the present invention with the sleeve connected to the sound. This figure shows the catheter tip and balloon (not shown) inserted into the sleeve 20. The circle around the sleeve 20 shows the orientation of FIGS. 13 and 14.

FIG. 13 is a partial section view of the balloon capture embodiment of the present invention in which the balloon is deflated. This figure shows the catheter tip 14 and balloon 15 inserted into the sleeve 20. It also shows a flange 21 that is integral to the sleeve 20 and that extends inward at the distal end of the sleeve. The purpose of the flange is to keep the catheter in place when the balloon is inflated, although in practice the friction created by the inflated balloon against the inner walls of the sleeve is sufficient to keep the catheter in place. FIG. 14 is a partial section view of the balloon capture embodiment of the present invention in which the balloon 15 is inflated. Both of these figures show the optional funnel 38 inside the threaded end 5 of the removable tip 3. The funnel 38 is intended to facilitate passage of a wire (used in connection with other embodiments described below) through the end of the sound and out the removable tip 3 and to prevent it from getting hung up in the tip of the sound.

An alternate balloon capture method (not shown) does not utilize a sleeve or pin. In this method, the sound is inserted through the patient's urethra into the bladder and out the abdominal wall, and the tip of the sound is removed. The catheter tip with the balloon is then inserted into the end of the sound from which the removable tip was removed, and the balloon is inflated. Inflation of the balloon while inside the sound creates sufficient friction to hold the catheter in place. The catheter and sound are then pulled out through the patient's urethra, and the balloon is deflated. The catheter and sound are separated, and the catheter is pulled back up into the patient's bladder. The balloon is re-inflated, and the catheter is attached to drainage.

FIGS. 15-19 illustrate the clamshell capture embodiment of the present invention. FIG. 15 is a perspective view of the clamshell capture embodiment of the present invention in which the clamshell is disengaged from the catheter and from the sound. This figure shows the catheter 13 and sound 1 with the tip (not shown) of the sound removed. It also shows a clamshell capture device 22 that comprises a top half and a bottom half. The top half of the clamshell capture device 23 comprises two pegs. One peg 23 passes through the lateral holes 16 in the catheter tip 14. The other peg 23 fits into a notch (not shown) in the bottom half of the clamshell capture device 23. The clamshell capture device has a threaded end 24 that fits into the threaded distal end of the sound.

FIG. 16 is a perspective view of the clamshell capture embodiment of the present invention in which the clamshell 22 is closed over the catheter 13 but not attached to the sound 1. FIG. 17 is a perspective view of the clamshell capture embodiment of the present invention in which the clamshell 22 is closed over the catheter 13 and attached to the sound 1. The circle around the clamshell 22 shows the orientation of FIGS. 18 and 19. Although the balloon 15 is shown in FIGS. 15-17, it is shown only for orientation purposes and is not necessary for this embodiment to function.

FIG. 18 is a section view of the clamshell and a partial section view of the catheter and sound. This figure shows the top and bottom halves of the clamshell 22 in relation to the catheter 13 and the sound 1. The top half of the clamshell comprises pegs 23, one of which passes through the lateral holes 16 in the catheter tip 14, and the other of which fits into a notch 25 in the threaded end 24 of the clamshell 22. FIG. 19 is a section view of the clamshell when it is closed over the catheter and attached to the sound (as shown in FIG. 17).

FIGS. 20-24 illustrate the sleeve capture embodiment of the present invention. FIG. 20 is a perspective view of the sleeve capture embodiment of the present invention in which the catheter is not inserted into the threaded extension of the sound, and the sleeve is not installed over the threaded extension of the sound. This figure shows the catheter 13, the sound 1, and a threaded extension 26 on the distal end of the sound. This figure also shows the sleeve 27 and pin 28. As shown in subsequent figures, the sleeve 27 is first placed over the catheter tip 14 and slid past the balloon 15, the catheter tip 14 is then inserted into the threaded extension 26 of the sound 1, and the pin 28 is inserted through the lateral holes 16 in the catheter tip 14 and through two holes 29 (only one of which is shown in FIGS. 20 and 21) the threaded extension 26. Lastly, the sleeve 27, which is threaded on the inside, is screwed onto and over the threaded extension 26.

FIG. 20A is a section view of the removable tip of the sound for use with the sleeve capture embodiment of the present invention. As shown in this figure, in order to accommodate the threaded extension 26 of the sound 1, the removable tip 37 of the sound is preferably longer than the removable tip shown in FIG. 3, and it is also threaded on the inside.

FIG. 21 is a perspective view of the sleeve capture embodiment of the present invention in which the catheter 13 is inserted into the threaded extension 26 of the sound 1, but the sleeve 27 is not installed over the threaded extension 26 of the sound 1. FIG. 22 is a perspective view of the sleeve capture embodiment of the present invention in which the catheter 13 is inserted into the threaded extension 26 of the sound 1, and the sleeve 27 is installed over the threaded extension 26 of the sound 1. The balloon 15 is shown in FIGS. 20 and 22 for orientation purposes but is not necessary for this embodiment to function.

FIG. 23 is a partial section view of the catheter inserted into the threaded extension of the sound and a section view of the sleeve positioned over the catheter but not over the threaded extension of the sound. This figure shows the catheter 13, the sound 1, and the sleeve 27 with inner threads. It also shows the catheter tip 14, the lateral holes 16 in the catheter tip 14, the threaded extension 26, and the holes 29 in the threaded extension. It also shows the pin 28 extending through the two lateral holes 26 in the catheter tip 14 and the two holes 29 in the threaded extension. FIG. 24 is a partial section view of the catheter tip 14 inserted into the threaded extension 26 of the sound 1 and a section view of the sleeve 27 positioned over the threaded extension 26 of the sound.

FIGS. 25-35 illustrate the ball-on-a-wire embodiment of the present invention. In this embodiment, a wire is passed through the urethral sound and inside the catheter, a ball is attached to the wire, the ball is pulled to the tip of the catheter, and the ball is used to guide the catheter to the tip of the sound.

Figure 25:
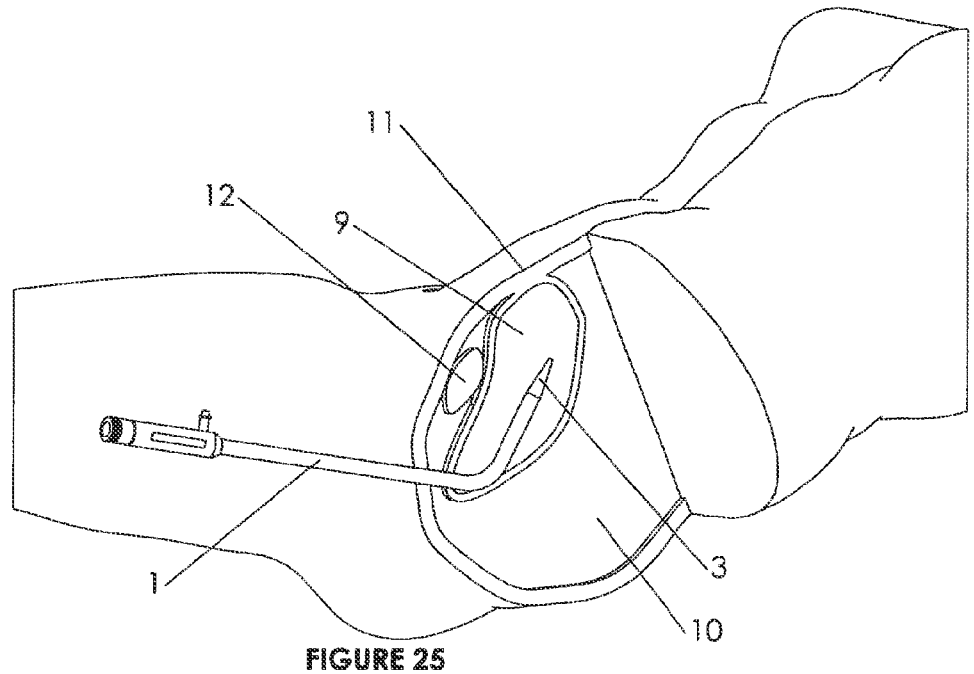
FIG. 25 is a section view of the urethral sound of the present invention inside the patient's bladder.
Figure 26:
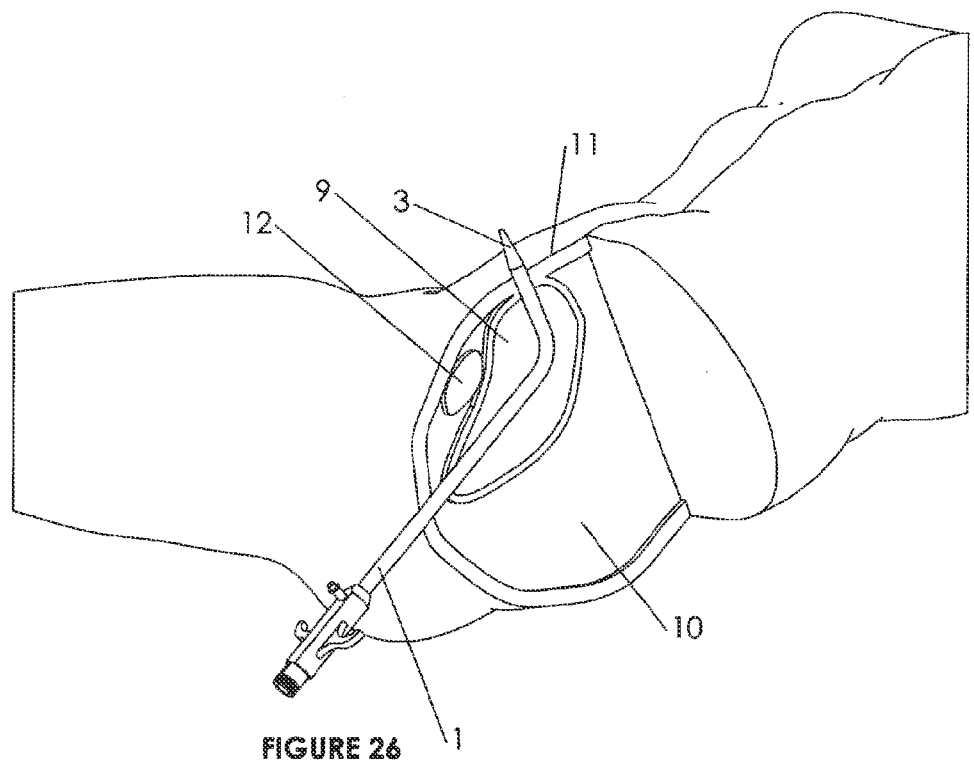
FIG. 26 is a section view of the urethral sound of the present invention after it has passed through the patient's abdominal wall.

FIG. 25 is a section view of the urethral sound 1 of the present invention inside the patient's bladder 9. FIG. 26 is a section view of the urethral sound 1 of the present invention after it has passed through the patient's abdominal wall 11. FIG. 27 is a section view of the urethral sound 1 of the present invention with a wire 30 passed through the sound. In practice, the wire will most likely be passed through the sound and held at the tip of the sound (so that it does not extend beyond the tip of the sound) as the sound is passed through the patient's urethra and bladder. The wire may then be advanced through the abdominal wall and act as a "guidewire" for the sound. Alternatively, the wire could be inserted into the sound after it has passed through the patient's urethra and bladder and out the abdominal wall. The wire is preferably similar to the Lunderquist-Ring torque guidewires or the Amplatz super-stiff guidewires, and the thickness of the wire may vary from approximately 0.10 to 0.20 centimeters. The distal end of the wire may be treated with polyvinyl pyrrolidine or another suitable substance so that it slides easily through the sound and through the urethra, bladder and abdominal wall.

FIG. 28 is a section view of the urethral sound 1 of the present invention with a wire 30 passed through the sound and a catheter 13 on the wire. At this stage in the procedure, enough wire is pushed through the sound so that the catheter can be placed on the wire. FIG. 29 is a partial perspective view of the ball 31 and wire 30. After the wire is passed completely through the catheter, a ball 31 is placed on the wire. The ball can be attached to the wire in a number of different ways. For example, the wire may be serrated, and a ball with matching grooves may be crimped over the serrations in the wire. Alternatively, the wire may have a small threaded section, the ball may be threaded on the inside, and the ball may be screwed over the threaded section of the wire so that it passes over the threaded section and onto the smooth portion of the wire beyond the threads. The ball with then move freely up and down the wire on only one side of the threaded section (because the threads only allow the ball to move in one direction) and will not be able to pass beyond the threaded section when the wire is being used to pull the catheter into the bladder. Although a ball is shown for illustrative purposes, any hook, nodule or similar object could be used. FIG. 30 is a section view of the urethral sound 1 of the present invention with a wire 30 passed through the sound and a catheter 13 and ball 31 on the wire. FIG. 31 is a partial perspective view of the ball 31 on the wire 30.

Next, the wire 30 is pulled back through the sound 1 until the ball 31 lodges in the tip 14 of the catheter 13. FIG. 32 is a section view of the urethral sound 1 of the present invention with a wire 30 passed through the sound, a catheter 13 and ball 31 on the wire, and the ball 31 pulled to the tip 14 of the catheter. FIG. 33 is a section view of the catheter tip 14 with the ball 31 on the wire 30 and inside the catheter tip.

Figure 34:
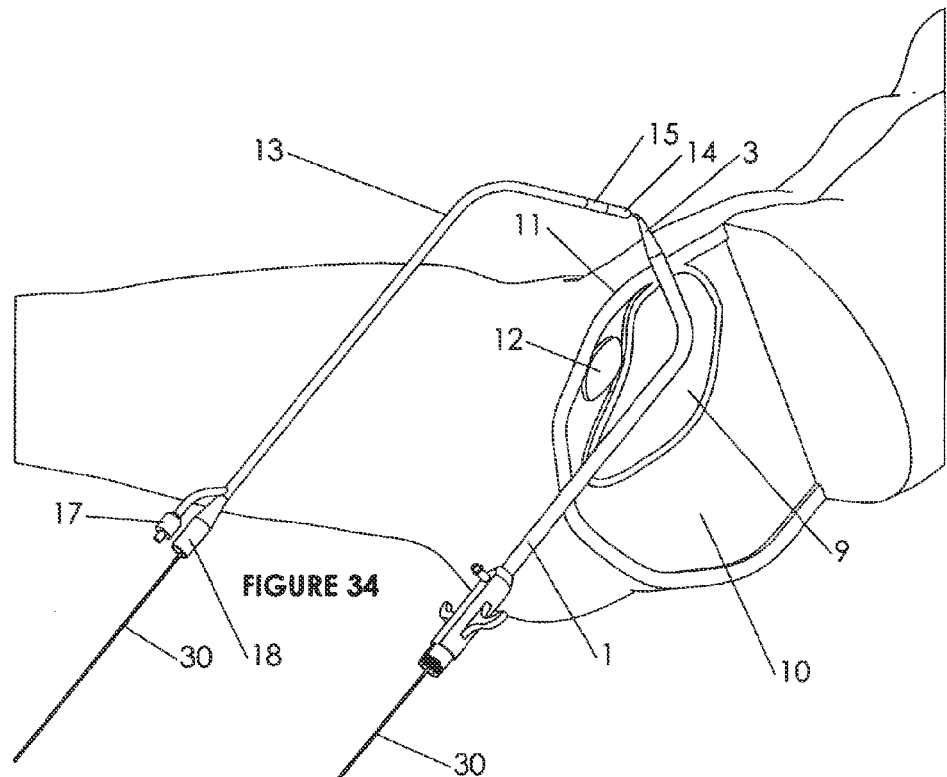
FIG. 34 is a section view of the urethral sound of the present invention with a wire passed through the sound, a catheter and ball on the wire, the ball pulled to the tip of the catheter, and the catheter tip pulled to the tip of the sound.

Next, the wire is pulled back through the sound 1 until the catheter tip 14 comes into contact with the tip 3 of the sound. FIG. 34 is a section view of the urethral sound 1 of the present invention with a wire 30 passed through the sound, a catheter 13 and ball 31 on the wire, the ball 31 pulled to the tip 14 of the catheter, and the catheter tip 14 pulled to the tip 3 of the sound. Next, the sound 1 is retracted (pulled inside the patient's body and into the bladder), and the catheter 13 is guided by the ball 31 on the wire 30 into the patient's bladder 9, with the catheter tip 14 in contact with the tip 3 of the sound.

Figure 35:
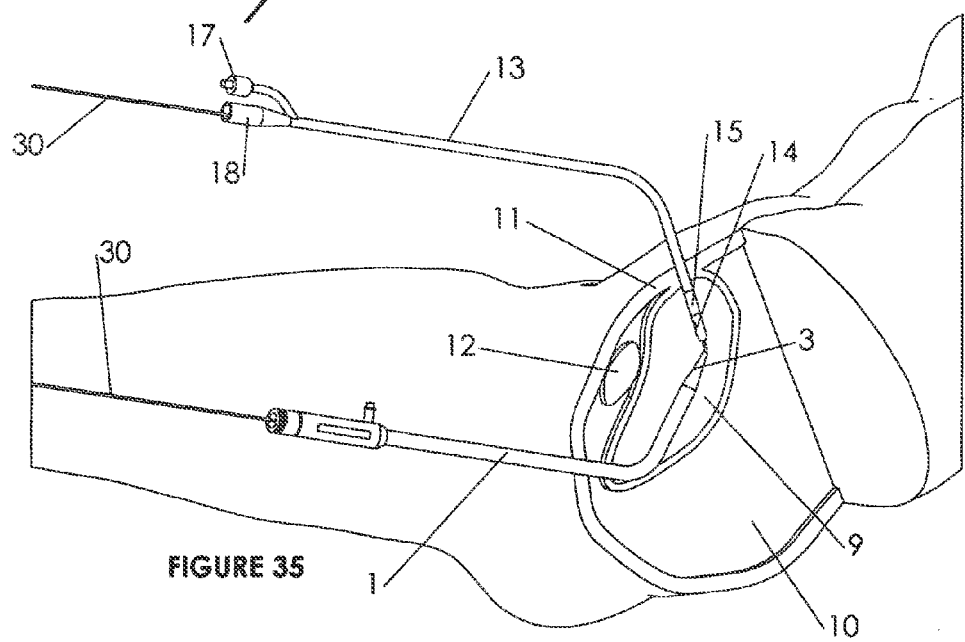
FIG. 35 is a section view of the urethral sound of the present invention with a wire passed through the sound, a catheter and ball on the wire, the ball pulled to the tip of the catheter, the catheter tip pulled to the tip of the sound, and the catheter pulled into the bladder.

FIG. 35 is a section view of the urethral sound 1 of the present invention with a wire 30 passed through the sound, a catheter 13 and ball 31 on the wire 30, the ball 31 pulled to the tip 14 of the catheter, the catheter tip 14 pulled to the tip 3 of the sound, and the catheter 13 pulled into the bladder 9. Once the catheter is in the desired position inside the bladder, the sound 1 is completely withdrawn through the patient's urethra, and the wire 30 is removed by pulling it out through the proximal end of the catheter (the end with the inflation member 17 and drainage connection 18). The balloon 15 is then inflated to keep the catheter in place inside the bladder 9.

Although the sound is shown in FIGS. 27-28, 30, 32, and 34-35 with the removable tip, in practice it may be desirable to remove the tip of the sound before the catheter is placed on the wire. That way, the catheter tip and balloon may be inserted into the end of the sound from which the removable tip was removed, and the balloon may be inflated inside the rigid walls of the sound, thereby providing additional stability for the catheter as it is pulled into the patient's bladder.

Figure 36:
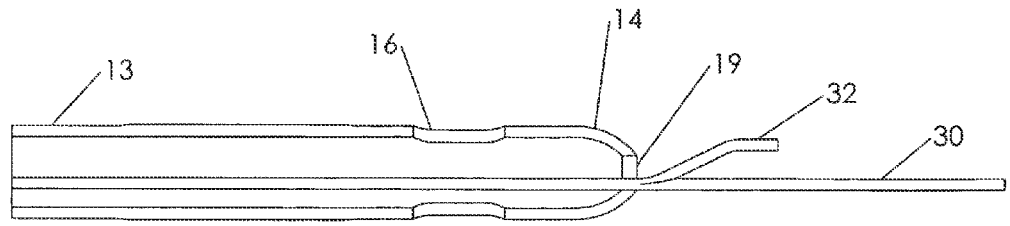
FIG. 36 is a section view of the catheter on a wire with a hook.

FIGS. 36-39 illustrate an alternate method of capturing the catheter on the wire. The procedure is the same as depicted in FIGS. 25-35, but a hook is used instead of a ball. FIG. 36 is a section view of the catheter 13 on a wire 30 with a hook 32. FIG. 36 illustrates one possible hook shape, but the present invention is not limited to any particular hook shape. If this particular type of hook is used, then it can be present on the wire before the wire is inserted through the sound and into the catheter. With other hook designs, the hook may need to be attached to the wire after the wire has passed through the sound and through the catheter, as discussed in connection with the ball-on-a-wire embodiment.

Figure 37:
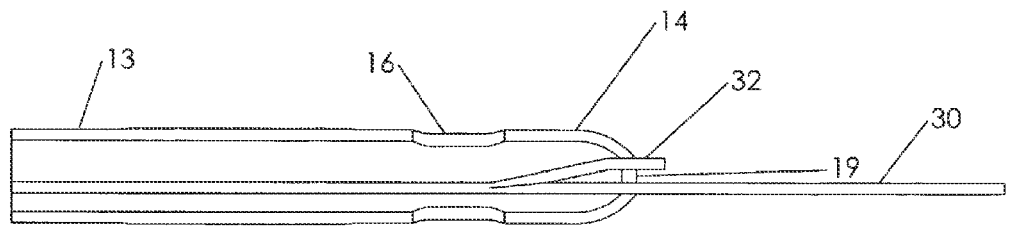
FIG. 37 is a section view of the catheter on a wire with the hook as it passes through the circular hole in the catheter tip.
Figure 38:
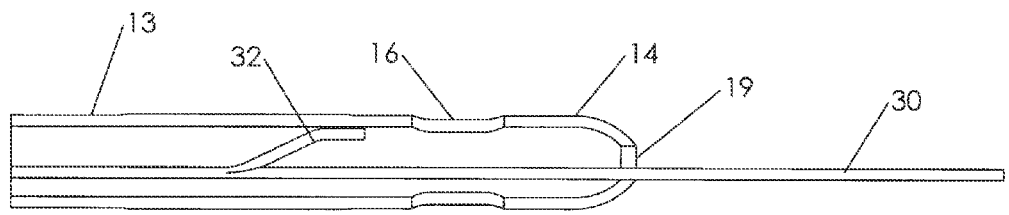
FIG. 38 is a section view of the hook after it has passed through the circular hole in the catheter tip and into the inside of the catheter.
Figure 39:
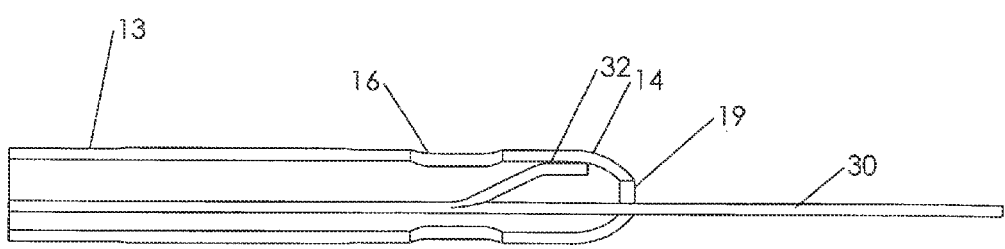
FIG. 39 is a section view of the hook on the wire as the wire is being pulled back through the sound.

FIG. 37 is a section view of the catheter 13 on a wire 30 with the hook 32 as it passes through the circular hole 19 in the catheter tip 14. FIG. 38 is a section view of the hook 32 after it has passed through the circular hole 19 and into the inside of the catheter 13. FIG. 39 is a section view of the hook 32 on the wire 30 as the wire is being pulled back through the sound (not shown). The hook 32 lodges in the catheter tip 14, thereby capturing the catheter so that it can be pulled toward the tip of the sound (not shown) and into the patient's bladder.

In yet another variation of the ball-on-a-wire and hook-on-a-wire embodiments, the wire can simply be crimped after the catheter is placed on the wire, such that the crimp serves the same purpose as the ball or hook.

Figure 40:
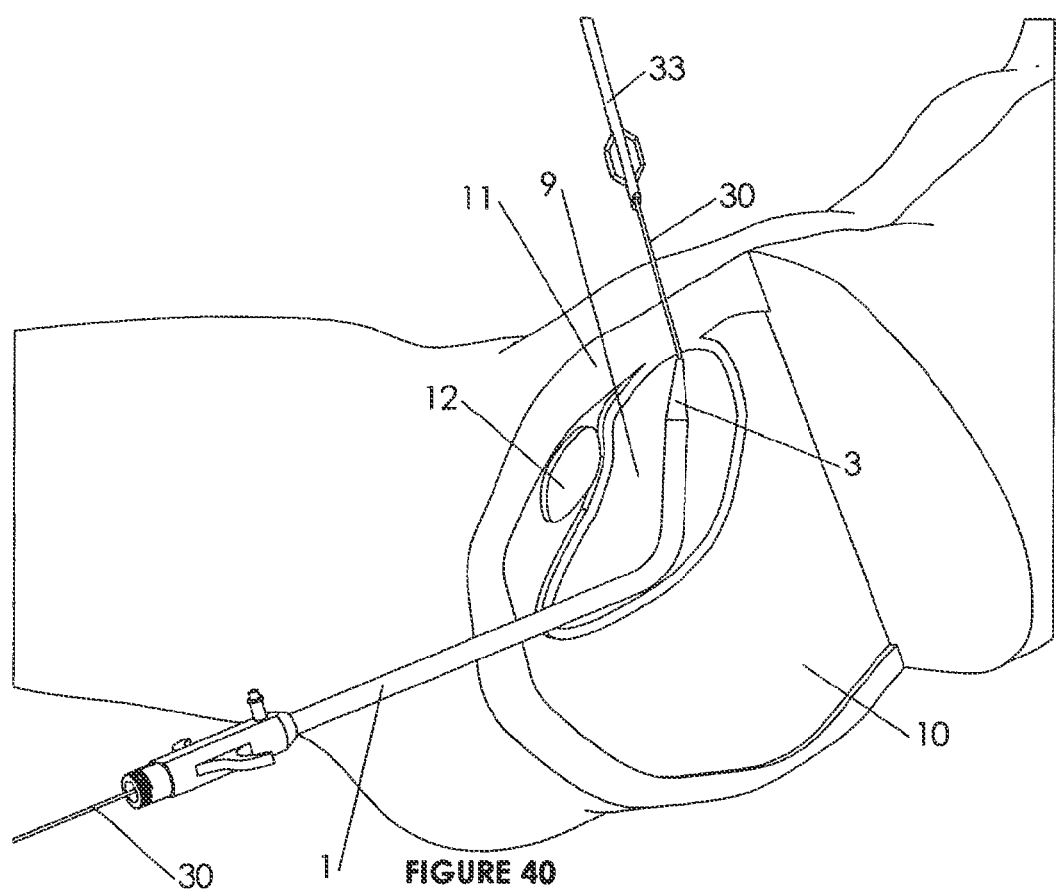
FIG. 40 is a section view of the knife on a wire.
Figure 41:
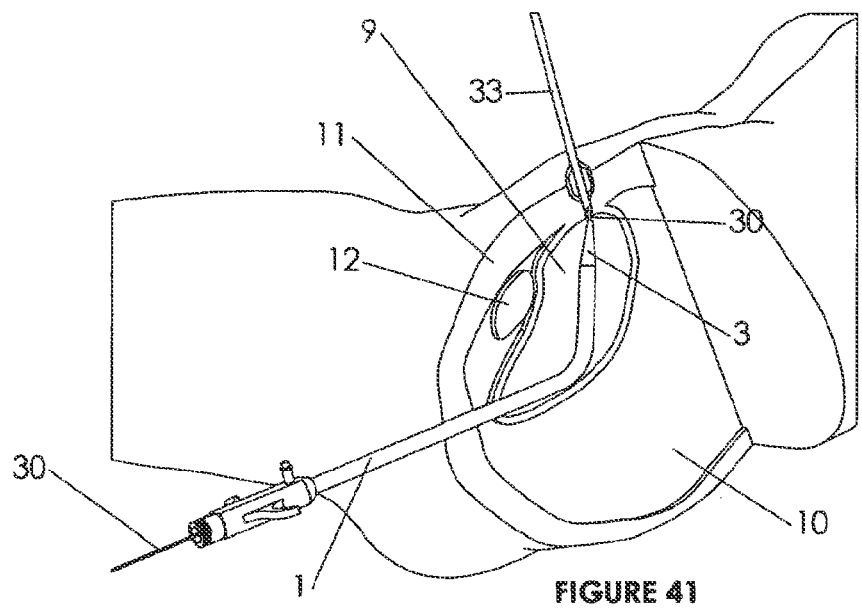
FIG. 41 is a section view of the knife on a wire with the tip of the knife in contact with the tip of the sound.

FIGS. 40-43 illustrate a number of different cutting tools that can be used in connection with the ball-on-a-wire (or hook-on-a-wire) procedure when the patient is so obese that the physician cannot get the tip of the sound to pass through the abdominal wall from the inside-out. FIG. 40 shows a knife 33 on the wire 30. In this procedure, the knife 33 is placed onto the wire 30 after the wire is passed out through the patient's abdomen. The knife 33 is then guided by the wire 30 as it is pushed through the abdominal wall 11. When the knife 33 comes into contact with the tip 3 of the sound, as shown in FIG. 41, the sound 1 is pulled back slightly and the knife 33 is pushed down again until it comes into contact with the tip 3 of the sound. This procedure ensures a uniform cut where the tip of the sound was when the knife first came into contact with it. The knife 33 is then removed from the wire 30, and the catheter is placed onto the wire and guided into the bladder using one of the methods described above (FIGS. 25-39).

Figure 40A:
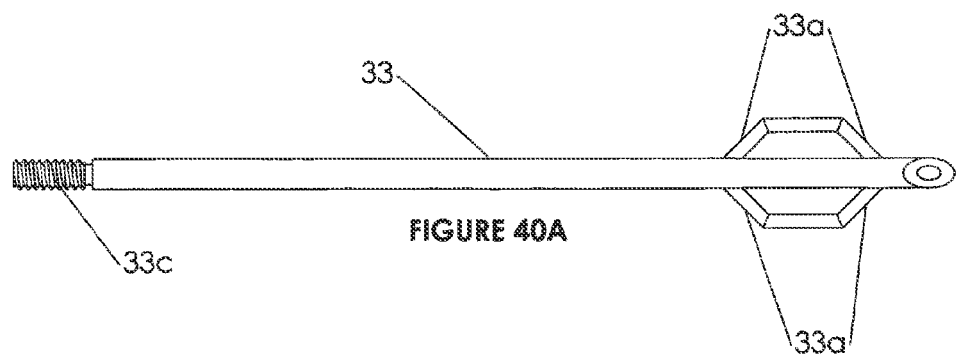
FIGS. 40A and 40B are side views of two alternate embodiments of the knife.
Figure 40B:
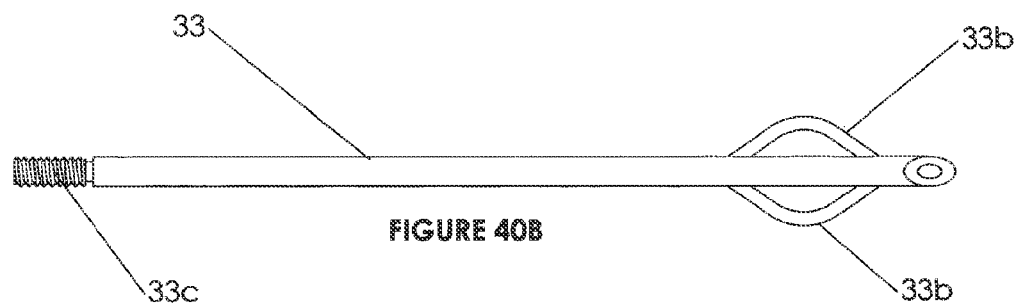
Figure 40C:
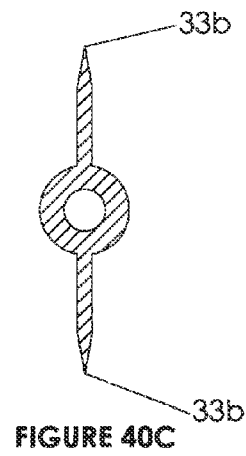
FIG. 40C is a section view of the knife, showing the cut made by the knife blades.

FIGS. 40A and 40B are side views of two alternate embodiments of the knife. As shown in these figures, the knife 33 comprises a leading edge 33a, which is sharp, and a threaded end 33c. The threaded end allows an extension to be added to the knife for extra length. The knife also comprises blades 33b, which may be shaped either as shown in FIG. 40A or FIG. 40B. In the preferred embodiment, there are two knife blades 33b, which are oriented so that there is a 180-degree spacing between them. In FIG. 40A, the knife blades 33b form a hexagon shape, whereas in FIG. 40B, they form a diamond shape. FIG. 40C is a section view of the knife, showing the cut made by the knife blades 33b. Other than in claims 32 and 33, the present invention is not limited to any particular shape of the knife or knife blades.

Figure 42:
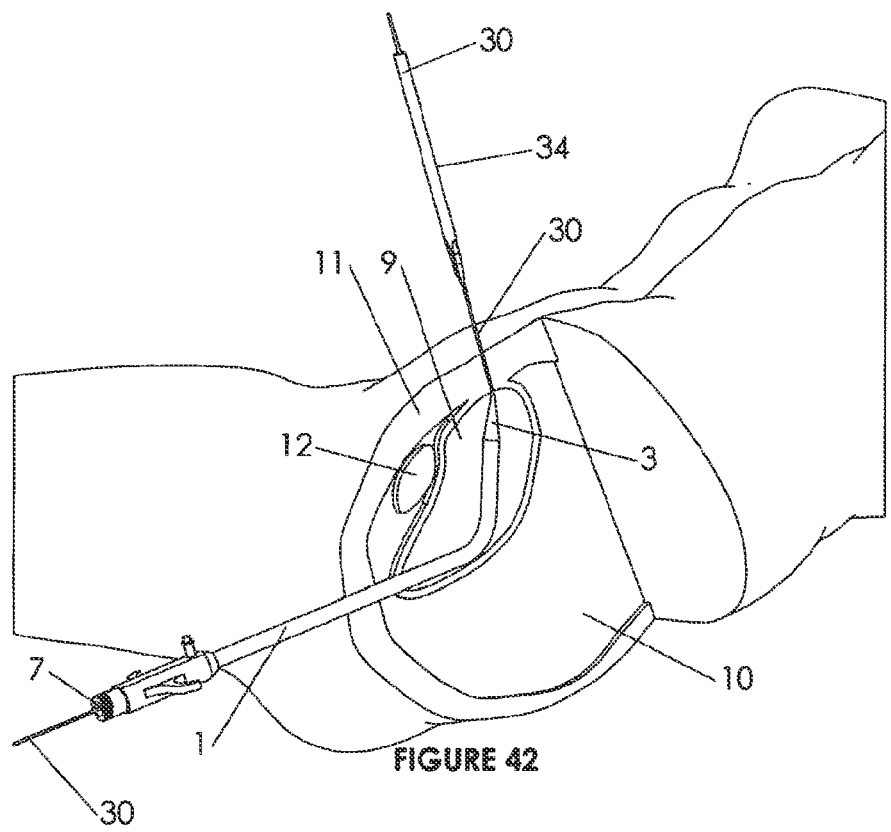
FIG. 42 is a section view of the trocar on a wire.
Figure 43:
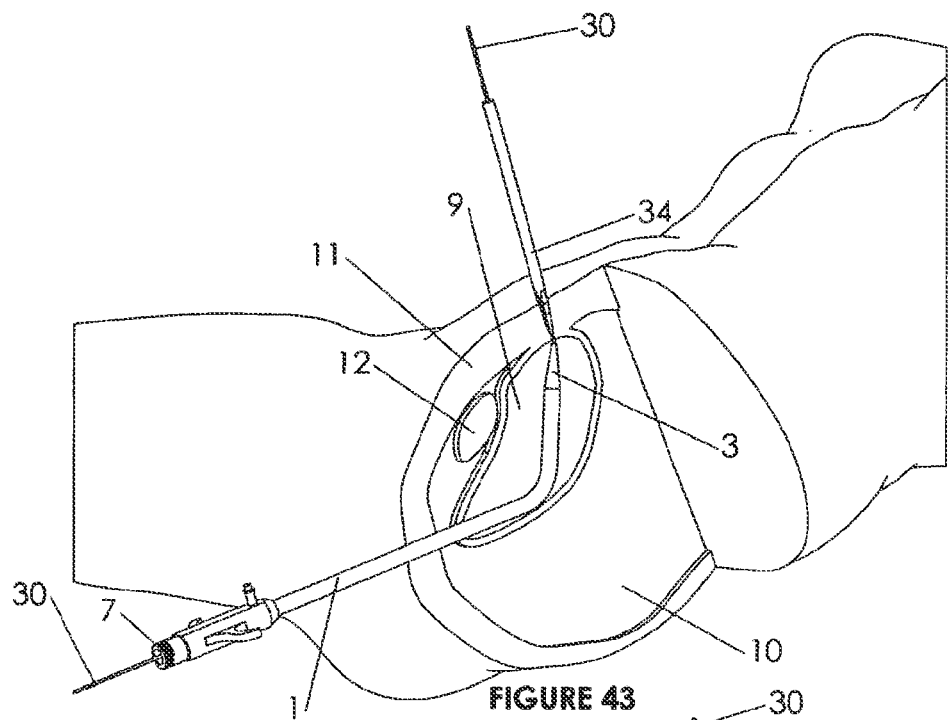
FIG. 43 is a section view of the trocar on a wire with the tip of the trocar in contact with the tip of the sound.

As shown in FIGS. 42 and 43, a trocar 34 may be used in lieu of a knife for a quicker and easier incision. The trocar 34 is loaded onto the wire and then pushed down until it makes contact with the tip 3 of the sound. FIG. 42A is a section view of the trocar. As shown in this figure, the trocar comprises trocar blades 34a on one end and inner threads 34b on the other end. The inner threads allow the trocar to be attached to an extension if greater length is needed. FIG. 42B is a perspective view of the trocar showing the scalloped blades. FIG. 42C is a section view of the trocar, showing the cut made by the trocar blades. The trocar provides a different type of cut than the knife due to the way it is shaped. The present invention is not limited to any particular shape of the trocar or trocar blades.

Figure 44:
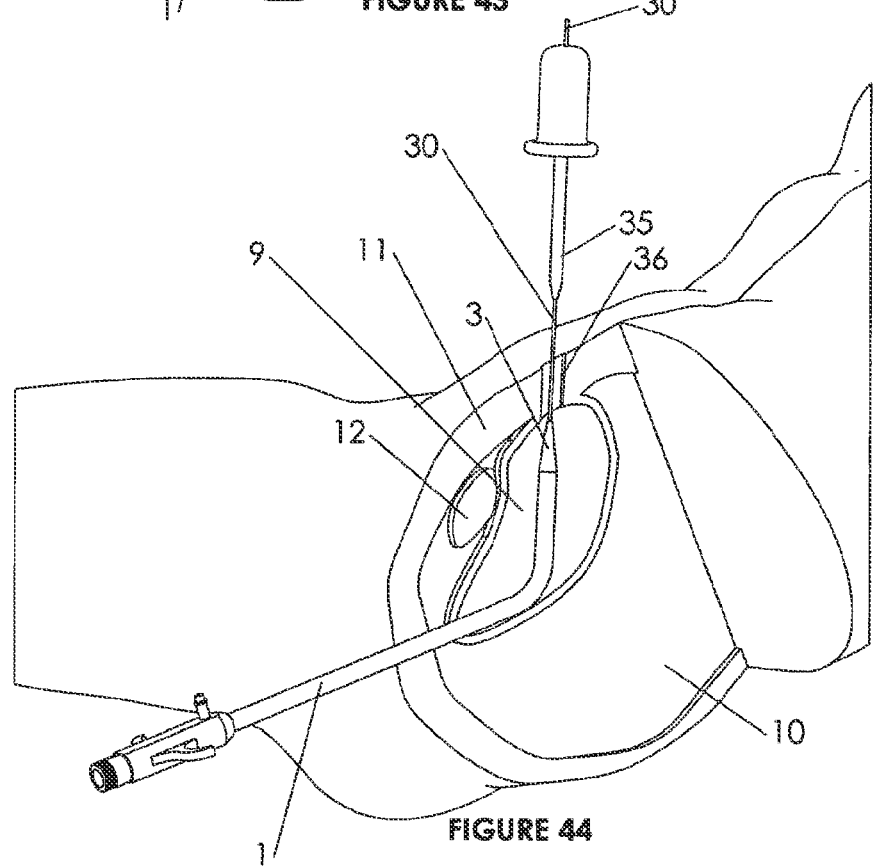
FIG. 44 is a section view of the screwdriver on a wire.
Figure 45:
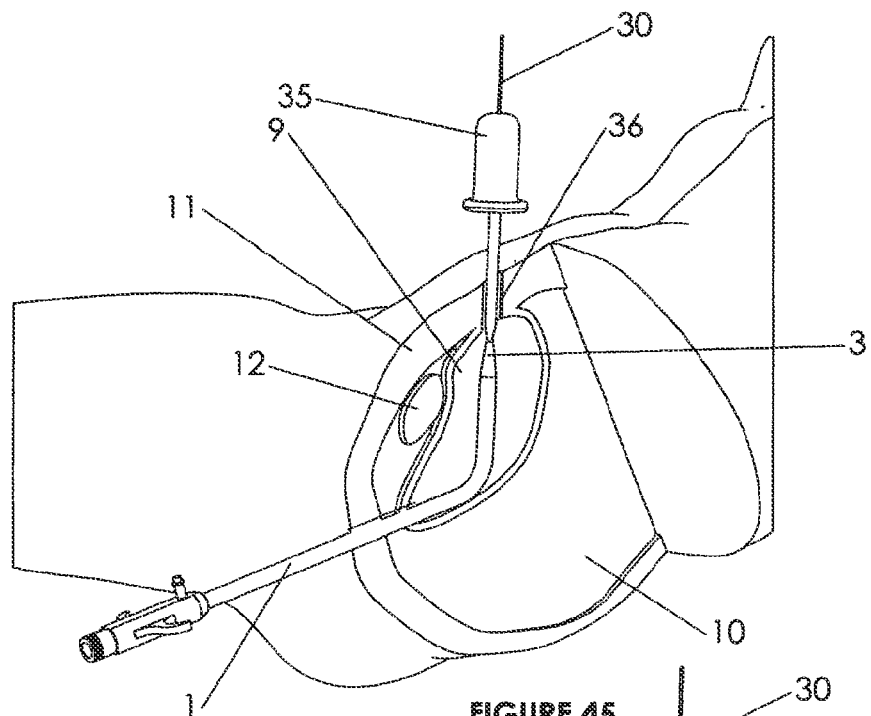
FIG. 45 is a section view of the screwdriver on a wire with the tip of the screwdriver in contact with the tip of the sound.
Figure 46:
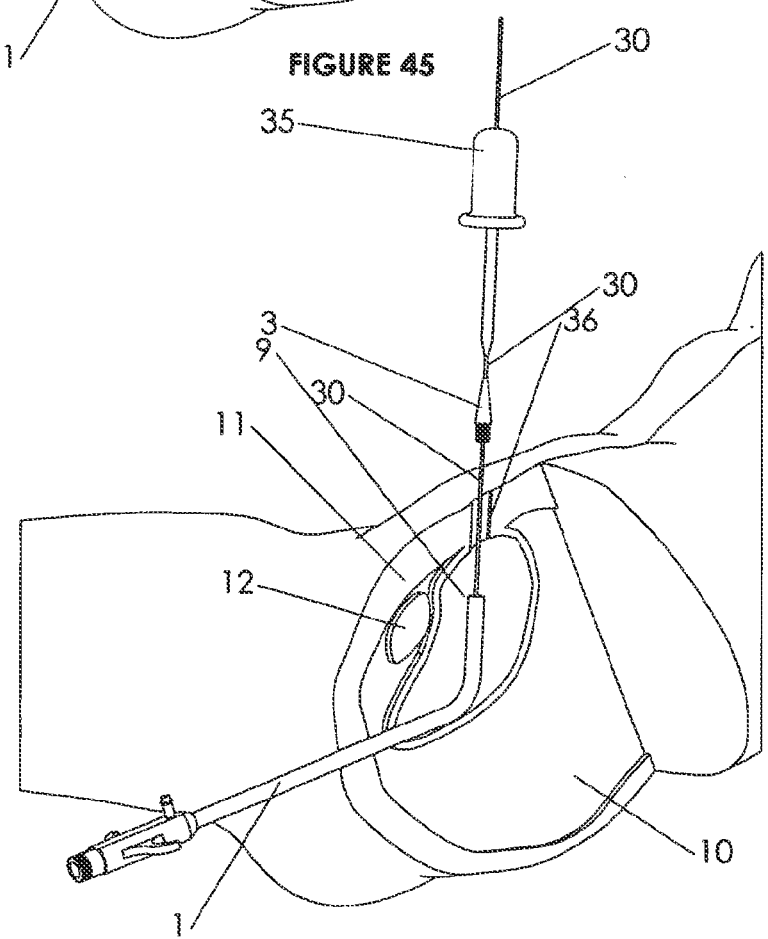
FIG. 46 is a section view of the screwdriver on a wire after the tip of the sound has been unscrewed from the sound.

FIG. 44 is a section view of the screwdriver on a wire. The screwdriver may be used whenever the tip of the sound will not reach the skin. The screwdriver enables the physician to remove the tip of the sound so that a catheter can then be inserted over the wire into the vacated distal end of the sound. As shown in this figure, the screwdriver 35 is placed onto the wire 30 after the wire is passed out through the patient's abdomen and after an incision 36 has been made with one of the cutting devices depicted in FIGS. 40-43. The screwdriver 35 is then guided by the wire 30 as it is pushed through the abdominal wall 11. When the screwdriver 35 comes into contact with the tip 3 of the sound, as shown in FIG. 45, the screwdriver is used to unscrew the removable tip 3 from the sound 1. In this procedure, a ball (not shown) or other nodule is placed on the wire and advanced to the tip of the sound so that the tip 3 can be removed from the patient's body by pulling the wire up through the incision site 36 after the tip 3 has been unscrewed, as shown in FIG. 46. Once the tip 3 is removed, the catheter (not shown) can be placed on the wire (as described in connection with the ball-on-a-wire, hook-on-a-wire and nodule-on-a-wire embodiments described above) and the catheter tip advanced into the distal end of the sound (the end from which the tip was removed). At that point, the balloon is inflated to assist with lodging the catheter inside the sound. The catheter and sound are pulled back out through the urethra, the balloon is deflated, the wire with the nodule is pulled out the abdominal end of the sound, the catheter is separated from the sound, and the catheter is pulled back into the bladder. The balloon is then re-inflated to maintain the catheter in place, and the catheter is attached to drainage.

Obviously, many modifications and variations of the present invention are possible in light of the above teachings. It is, therefore, to be understood that within the scope of the appended claims, the invention may be practiced otherwise than as specifically described.

What is claimed:

1. Apparatus for creating a suprapubic surgical opening through an abdominal wall into a bladder and for placing a catheter in the surgical opening, comprising in combination:
   a hollow urethral sound having a distal end adapted for insertion within a urethra and the bladder and a proximal end adapted to remain outside of the urethra by which to manipulate the distal end of the sound within the bladder, the distal end of the sound having a sound tip;
   a wire having proximal and distal ends and movably positioned within the sound to selectively extend the distal end of the wire from the sound tip sufficiently to penetrate from the bladder through the abdominal wall and to expose an external portion of the distal end of the wire outside of the abdominal wall and to selectively retract the distal end of the wire toward the sound tip, the distal end of the wire which penetrates from the bladder through the abdominal wall establishing a path for the surgical opening;
   a cutting tool adapted to create the surgical opening by movement along the path of the wire through the abdominal wall and into the bladder to the sound tip, the cutting tool adapted to be moved out of the surgical opening along the path of the wire after creating the surgical opening, the cutting tool adapted to be connected outside of the abdominal wall for guidance along the path of the wire and adapted to be removed from the path of the wire from the outside of the abdominal wall after creating the surgical opening;
   the catheter having a distal end and a proximal end and a hollow portion extending between the distal end and the proximal end, the distal end of the catheter adapted to be placed through the surgical opening and into the bladder, the proximal end of the catheter adapted to remain outside of the surgical opening and the abdominal wall, and the hollow portion adapted to conduct liquid from the distal end of the catheter within the bladder to the proximal end of the catheter outside of the surgical opening and the abdominal wall, the distal end of the catheter including a catheter tip and an inflatable balloon; and
   a connector for connecting the catheter tip to the external portion of the distal end of the wire outside of the abdominal wall and for disconnecting the catheter tip from the distal end of the wire when the distal end of the catheter is located within the bladder;
   the connector permitting the distal end of the catheter to be guided from outside the abdominal wall through the surgical opening and into the bladder upon retraction of the wire within the sound;
   the connector permitting the balloon to be inflated within the bladder while the distal end of the wire remains connected to the catheter tip within the bladder; and
   the connector permitting drainage of liquid in the bladder from the distal end of the catheter through the hollow portion to the proximal end of the catheter while the distal end of the wire remains connected to the catheter tip within the bladder.

2. Apparatus as defined in claim 1, wherein:
   the distal end of the wire is extended and retracted by manipulation of the proximal end of the wire at the proximal end of the sound.

3. Apparatus as defined in claim 1, wherein:
   the cutting tool slides along the path of the wire to create the surgical opening.

4. Apparatus as defined in claim 3, wherein:
   the cutting tool includes an opening through into which the distal end of the wire is inserted to connect the cutting tool to the wire.

5. Apparatus as defined in claim 1, wherein:
   the cutting tool includes a trocar.

6. Apparatus as defined in claim 1, wherein:
   the cutting tool includes a knife.

7. Apparatus as defined in claim 1, wherein:
   the connector includes a rotatable portion.

8. Apparatus as defined in claim 1, wherein:
   the connector includes a threaded portion.

9. Apparatus as defined in claim 1, wherein:
   the connector comprises a object on the wire which is removably lodged in the catheter tip.

10. Apparatus as defined in claim 9, wherein:
    the object is a ball.

11. Apparatus as defined in claim 9, wherein:
    the object is a nodule.

12. Apparatus as defined in claim 9, wherein:
    the object is a hook.

13. Apparatus as defined in claim 9, wherein:
    the object is a crimp in the wire.

* * * * *